(12) United States Patent
Epley

(10) Patent No.: US 7,892,180 B2
(45) Date of Patent: Feb. 22, 2011

(54) HEAD-STABILIZED MEDICAL APPARATUS, SYSTEM AND METHODOLOGY

(75) Inventor: John M. Epley, Portland, OR (US)

(73) Assignee: Epley Research LLC, Portland, OR (US)

( * ) Notice: Subject to any disclaimer, the term of this patent is extended or adjusted under 35 U.S.C. 154(b) by 0 days.

(21) Appl. No.: 11/714,459

(22) Filed: Mar. 5, 2007

(65) Prior Publication Data

US 2007/0161875 A1 Jul. 12, 2007
US 2010/0041961 A9 Feb. 18, 2010

Related U.S. Application Data

(62) Division of application No. 10/715,871, filed on Nov. 17, 2003.

(60) Provisional application No. 60/427,484, filed on Nov. 18, 2002.

(51) Int. Cl.
*A61B 5/00* (2006.01)
*A61B 13/00* (2006.01)
*A61B 5/103* (2006.01)
*A61B 5/117* (2006.01)
*A61M 31/00* (2006.01)

(52) U.S. Cl. .................. 600/559; 600/552; 600/558; 600/560; 600/561; 600/587; 600/595

(58) Field of Classification Search .............. 600/300, 600/301, 372, 382, 384, 393, 522, 552, 559, 600/560, 561, 587, 595, 558
See application file for complete search history.

(56) References Cited

U.S. PATENT DOCUMENTS 3,258,008 A 6/1966 Vulliet-Durand
3,583,794 A 6/1971 Newman
3,716,046 A 2/1973 Janeke et al.
4,014,320 A 3/1977 Richards
4,029,083 A 6/1977 Baylor
4,102,564 A 7/1978 Michael (Continued)

FOREIGN PATENT DOCUMENTS

AU 682908 5/1995

(Continued)

OTHER PUBLICATIONS

O'Leary, Diagnostic Screening with the Vestibular Autorotation Test (VAT), Audiology Online, Oct. 2002, (6 pages) www.4wsr.com/vat.htm, San Antonio, USA.

(Continued)

*Primary Examiner*—Jeffrey G Hoekstra
(74) *Attorney, Agent, or Firm*—James G. Stewart PC

(57) ABSTRACT

Structure and methodology involving mountable and head-wearable frame structure which is positionally stabilized, during use, relative a human subject's head, and which carries a selection of positionally anchored data sensors, and stimuli deliverers, that are relevant to the diagnosis and treatment of vestibular disorders. Special configurations are provided for two types of stimulators, one for sound application and air-pressure modification, and the other for the introduction of fluids to the ear. Stabilization enables tight and accurate correlation of data which is quickly analyzable by a connected, properly algorithmed computer, which can also be used for feedback control in a designed "expert" system. The invention enables, among other things, practical and significant differentiation between physiological and pathological nystagmus.

17 Claims, 7 Drawing Sheets

U.S. PATENT DOCUMENTS

| | | | |
|---|---|---|---|
| 4,320,768 A | 3/1982 | Ledley et al. | |
| 4,474,186 A | 10/1984 | Ledley et al. | |
| 4,698,564 A | 10/1987 | Slavin | |
| 4,710,128 A | 12/1987 | Wachsmuth et al. | |
| 4,738,269 A | 4/1988 | Nashner | |
| 4,757,807 A | 7/1988 | Densert et al. | |
| 4,815,839 A * | 3/1989 | Waldorf | 351/210 |
| 4,817,633 A | 4/1989 | McStravick et al. | |
| 4,818,097 A | 4/1989 | Linde | |
| 4,830,024 A | 5/1989 | Nashner et al. | |
| 4,988,183 A | 1/1991 | Kasahara et al. | |
| 5,042,910 A | 8/1991 | Dolezal | |
| 5,285,685 A | 2/1994 | Chelette | |
| 5,303,715 A | 4/1994 | Nashner et al. | |
| 5,421,818 A | 6/1995 | Arenberg | |
| 5,474,529 A | 12/1995 | Arenberg | |
| 5,476,446 A | 12/1995 | Arenberg | |
| 5,517,021 A | 5/1996 | Kaufman et al. | |
| 5,621,424 A | 4/1997 | Shimada et al. | |
| 5,900,849 A * | 5/1999 | Gallery | 345/8 |
| 5,942,954 A | 8/1999 | Galiana et al. | |
| 6,045,528 A | 4/2000 | Arenberg et al. | |
| 6,159,171 A | 12/2000 | Densert et al. | |
| 6,314,324 B1 | 11/2001 | Lattner et al. | |
| 6,795,780 B1 | 9/2004 | Hyde | |
| 6,800,062 B2 | 10/2004 | Epley | |
| 6,820,037 B2 | 11/2004 | Simon | |
| 7,041,063 B2 | 5/2006 | Abreu | |
| 7,469,162 B2 | 12/2008 | Lattner et al. | |
| 7,559,766 B2 | 7/2009 | Epley | |
| 2002/0151818 A1 | 10/2002 | Watt et al. | |
| 2004/0097839 A1 | 5/2004 | Epley | |
| 2005/0122477 A1 | 6/2005 | Alster et al. | |
| 2005/0165323 A1 | 7/2005 | Montgomery et al. | |
| 2005/0240253 A1 | 10/2005 | Tyler et al. | |

OTHER PUBLICATIONS

Hoekstra, Jeffrey, Office Action for U.S. Appl. No. 10/715,871 issued Mar. 27, 2009 by USPTO.

Hoekstra, Jeffrey, Office Action for U.S. Appl. No. 10/715,871 issued Dec. 29, 2009.

International Preliminary Report on Patentability for Int'l Patent App. No. PCT/US07/12953; Dec. 29, 2008 (10 pages.

O'Leary, Diagnostic Screening wtlh the Vestibular Autorotation Test (VAT), Audiology online, Oct. 2002, www.4wsr.com/vat.htm, San Antonio, TX USA (6 pages).

International Preliminary Report on Patentability for Int'l Patent App. No. PCT/US04/13951; Apr. 18, 2006 (8 pages).

\* cited by examiner

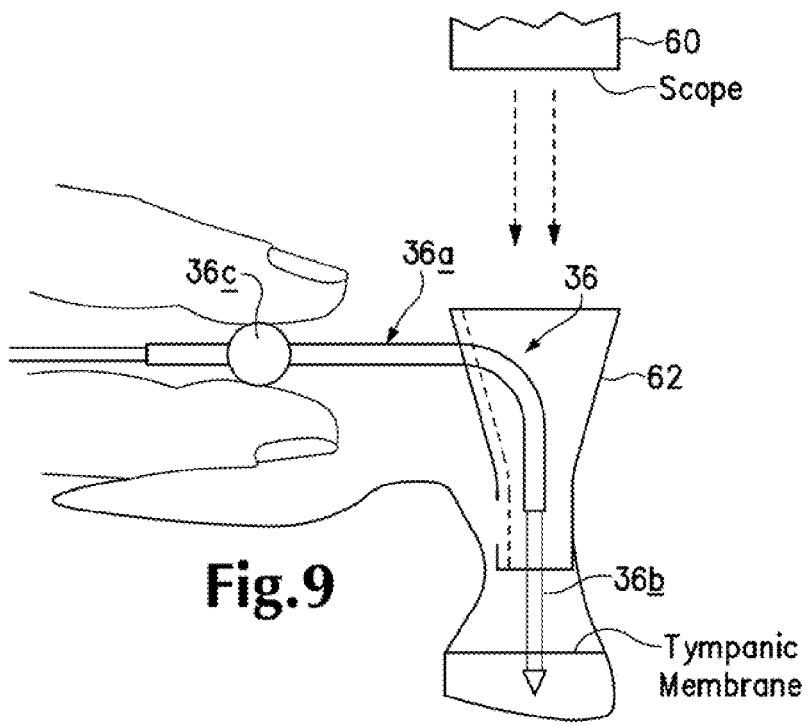
Insert trocar thru TM under direct view of scope, guiding by rolling bead between fingers. Handle fits thru slot in speculum.
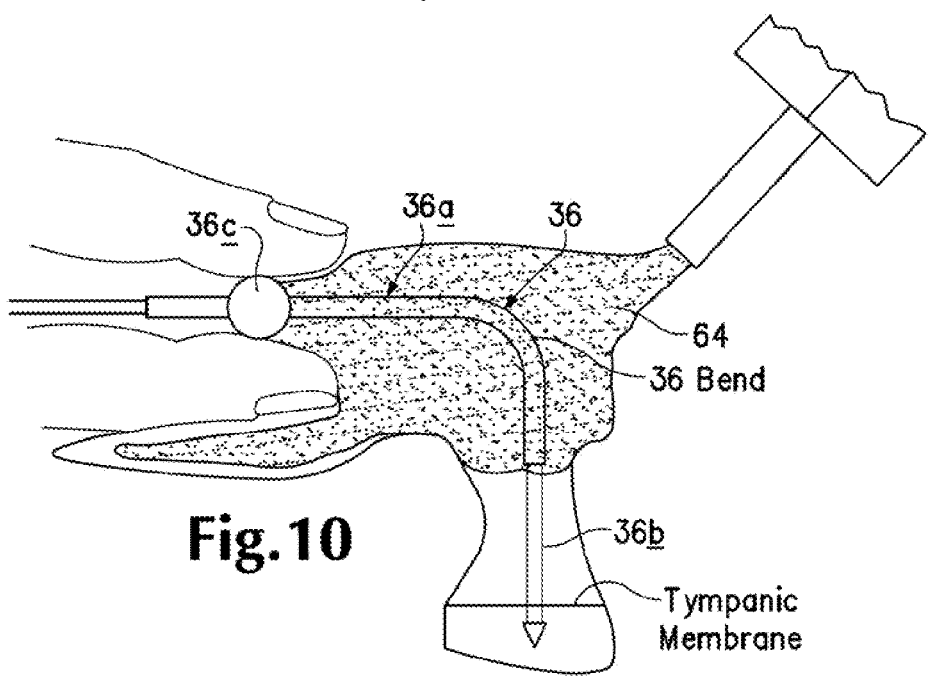
With fingers braced against head to stabilize trocar, remove speculum and inject molding material into area.

HEAD-STABILIZED MEDICAL APPARATUS, SYSTEM AND METHODOLOGY

RELATED APPLICATIONS

This application is a Divisional of U.S. patent application Ser. No. 10/715,871, entitled HEAD-STABILIZED MEDICAL APPARATUS, SYSTEM AND METHODOLOGY, filed 17 Nov. 2003, the disclosure of which is herein incorporated by reference in its entirety, which itself claims the benefit of priority to provisional application 60/427,484 filed on Nov. 18, 2002.

This invention was made with government support under PHS 398/2590 awarded by the National Institutes of Health. The government has certain rights in the invention.

BACKGROUND AND SUMMARY OF THE INVENTION

The present invention involves a head-stabilized method and apparatus designed for the diagnosis and treatment of vestibular disorders involving symptoms of dizziness, vertigo and/or imbalance. It also relates to the structures of certain special devices that are particularly suited for use with this method and apparatus, and to certain procedural approaches that the structure and method of the invention make advantageous.

In a manner of speaking, the invention recognizes, and centers attention on, the discovered significance of utilizing various, plural-simultaneously-employed sensors/detectors which are specially positionally stabilized, both (a) with respect to the head of a patient, and (b) with respect to each other, for the simultaneous gathering, and immediate computer processing, of plural-parameter data which can lead to accurate diagnoses and treatment of disorders of the types just generally mentioned above. Both mentioned categories of stabilization have been found to be important and unique in this sophisticated and challenging field of medical practice. Positional stabilization, undertaken in accordance with practice of the invention, leads to accurate correlation of different simultaneously gathered data components, and thus leads, in turn, to significant improvements in diagnostic speed and accuracy, and in trustable opportunities to rely with confidence on rapid, computer-based vestibular analyses and conclusions.

Dizziness, including vertigo and imbalance, is one of the most common complaints presenting to the physician. Although these symptoms may be caused by a variety of abnormal conditions affecting either the peripheral or central nervous systems, the cause can most commonly be traced to abnormalities involving the vestibular endorgans in the inner ear, or, less frequently, to their associated neural pathways to and within the brain. The vestibular endorgans are actually mechanico-transducers that normally sense, as information, either angular or linear acceleration of the head. This information is relayed, either through reflex, or after central integration with somatosensory and visual information, to the eyes (vestibular ocular reflex) (VOR) or the muscles of postural control (vestibulo-spinal reflex) (VSR). Thus, diagnosis and treatment of these disorders has been very dependent upon the ability to observe and quantify the reflex output of these systems, or the behavioral response thereto, thus leading to the localization of pathology and treatment directed thereto.

The anatomical sensors of angular acceleration, which provide the percept of rotation in space in any plane, are the semicircular canals which are located with three on each side within the inner ear, oriented orthogonally to each other. Each semicircular canal acts as a sensor of rotation in the plane of its orientation. It contains fluid that, due to its inertia, lags angular accelerations or decelerations of the head in the plane of the canal, and thereby actuates a sensor of fluid displacement, the cupula. This activation provides information via neural pathways to the brain stem, which information is carried via a reflex arc to the eye muscles, called the vestibuloocular reflex. During angular movements of the head, this reflex keeps the eyes oriented in space via a counter-rotation until the eyeball reaches a certain point, whereupon there is a quick correction in the opposite direction called a saccade. When such activity is repetitive, what results is an involuntary jerking motion of the eyes, called nystagmus, which occurs in the plane of the semicircular canals that generate it. By observing such nystagmus under various conditions, one can determine whether the semicircular canals are functioning normally and, if not, which canal is dysfunctional. One can also often determine the nature of the dysfunction. Also, the nystagmus behavior can be followed in the course of treatment, thus to monitor effectiveness. Dysfunction of the semicircular canals results mainly in symptoms of vertigo. The cause of dysfunction can be neurological or mechanical.

Quantitative assessment of the VOR and other eye movements under various conditions is carried out in a standard battery of tests known as nystagmography. When eye electrodes are used to detect eye movement, it is called electronystagmography (ENG). When video technology is used to detect eye movement, it is called videonystagmography (VNG). Testing is usually carried out in a light-obscuring environment in order to minimize the effects of optic fixation on the suppression of nystagmus. To varying degrees, nystagmus can also be suppressed by lack of alertness, by certain drugs, and by and habituation.

The standard ENG/VNG test battery includes a few standard head positions that are intended to provide an analysis of positional vertigo. However, these standardized test positions do not employ the ideal anatomical positions for obtaining useful information. Thus, new methods of investigating the causes of positional nystagmus and vertigo call for new standard positions for screening purposes, plus the triggering of more definitive tests when indicated. In addition, nystagmus data is typically acquired and analyzed in small segments which completely ignore nystagmus occurring during intervening periods and transition moves. Inasmuch as nystagmus occurring in a particular test position will be dependent upon numerous factors, such as (a) the rapidity and method of the just-mentioned maneuver, (b) the time lapse after a test position is reached until the data-acquisition run is commenced, and (c) the exact angles of the test positions, etc, the usual ENG/VNG test battery, as now generally carried out, is not optimally effective and accurate.

What is needed, and is definitively provided, among other things, by the present invention, is a method of carrying out the indicated screening and selected tests that can be automated and programmed to carry out certain screening tests and, but that is (a) capable of interjecting certain more definitive tests when so indicated by the screening tests, (b) can perform tests that are physiologically more meaningful than those previously done, and useful in diagnosing and treating a subject, (c) can acquire real-time data in a continuum throughout a test session, (d) can distinguish between normal and abnormal nystagmus, and (e) can, through careful programming, accomplish these tasks in as short a time as possible. Means must also be available that selects, analyzes and displays acquired data in a brief, understandable, and reliable summary.

The anatomical sensors of linear acceleration, the otolithic organs called the utricle and saccule, are located on each side in the inner ear. Each is made up of a layer of heavy particles that is attached to hair cells that can, when stimulated, initiate a neural discharge. When the head is placed in various positions relative to gravity, or moves linearly in various directions, the resulting change in the inertio-gravitational vector acting upon the particles presents changing forces of strain that modulate the neural discharge of the attached hair cells. The resulting neural input leads to the brain stem, thence to the spinal nerves, and finally to the muscles of postural control in the vestibulo-spinal reflex. Simultaneously, at a higher level, there is a subjective sense of the inertio-gravitational vector, called graviception, that in a normal subject is accurate to within a few degrees.

Abnormal conditions adversely affecting the otolithic organs cause mainly symptoms and signs of imbalance. This imbalance of otolithic origin results from either unstable neural input from an otolithic organ, or organs, or a bilateral deficit. Unstable neural input results from otolithic function that is either recently reduced from the normal, or is distorted from the normal input. This distorted neural input usually results from aberrant receptivity of the otolithic organ to non-gravitational forces, such as sound and changing intralabyrinthine pressure. Central compensation generally takes place adequately over time for the reduced form if it is unilateral and becomes stable, but compensation is delayed or not forthcoming in response to the distorted form because of its persistent instability. Thus, the distorted form is by far the more common cause of chronic vertigo. It is seen frequently as the principal mechanism of post-traumatic vertigo.

Research by me and others has indicated that a quantifiable assessment of the distorted neural input arising as a consequence of aberrant receptivity of an otolithic organ can be accomplished by determining the adverse postural effects of either sound or a changing intralabyrinthine pressure, as can be ascertained in a standing subject by observing, directly or by measuring apparatus, an increase in sway or a tendency to fall. This is usually done through posturography with the subject standing on a force plate, but, uniquely with respect to the present invention, as will be seen, is done through gravitational and angular sensors, and an inclinometer (or inclinometers), which are appropriately stabilized on the head and with respect to one another.

A problem with analyzing adverse postural effects for this purpose is that test subjects are usually acutely aware of their recent postural misperceptions that have resulted in abnormal sway or fall in a particular direction, and can quickly compensate for these misperceptions to some degree when presented with the same apparent stimulus. Thus, if air pressure that is presented to an ear canal of a standing subject with eyes closed were to cause a sway, or a fall, in a particular direction, the next time the same stimulus is presented, that same subject will habitually tend to compensate by counteracting the sway or fall. This is because, on the first trial, the subject received somatosensory feedback from the feet and postural muscles indicating that involuntary sway, or a fall, in a particular direction, took place. This tendency to compensate results in limited repeatability, and thus, questionable reliability of such a test using postural control as a measure. This issue is addressed by the present invention largely in the form of presenting sound and pressure stimuli in an alternating, variable and random, computer-controlled fashion, rather than by presenting stimuli to one ear at a time, and in a predetermined manner. This novel method results in greater repeatability and reliability, and is discussed further below.

Many subjects with vertigo symptoms complain of aggravation of these symptoms by loud sound, or by conditions that are known to impart pressure change to the intralabyrinthine fluids. Aberrant receptivity of the labyrinth to sound or intralabyrinthine pressure change can occur in either the semicircular canals, thereby adversely impacting the VOR system and producing nystagmus, or in the otolithic organs, thereby adversely impacting the VSR system and producing abnormal postural effects and altered gravitational perception. The latter condition, involving the VSR system, occurs far more frequently, yet the most commonly used procedure in testing of the effect of sound or intralabyrinthine pressure change involves only observation of the eyes. Thus, in the commonly used method of performing Hennebert (pressure) test and Tullio (sound) tests, the subject is seated and the clinician observes the eyes, either directly or with the assistance of magnification or electronic means, for abnormal nystagmus, and thus the postural effect information is seldom sought. Given this, an improved method is needed for quantifying and localizing the effects of sound and intralabyrinthine pressure change on the VSR arc by monitoring their effects on postural control, which is basically a test of gravitational perception, because sound and pressure have been shown in these situations often to cause an altered perception of the inertio-gravitational vector.

In the present state-of-the-art, quantitative information on the status of both the VOR and the VSR requires two separate devices, taking up more space in the vestibular laboratory and adding to expense. In addition, several valuable existing tests have not been utilized significantly outside of research laboratories because of the expense involved in the equipment to perform each test separately. In the practice of the present invention, placement of multiple stimulus and response modalities in conditions stabilized to the head solves these problems.

One example of this is seen with vestibular lithiasis, or benign paroxysmal positional vertigo and different variants, whereby abnormal particles in the semicircular canals render the canals sensitive to linear acceleration, including gravitation, creating symptoms of vertigo in response to position change of the head relative to gravity. These conditions are very common, and can often be improved or corrected by repositioning maneuvers, whereby the particles are moved, via a particular sequential positioning of the subject's head with optional induced head oscillation, to an area of the labyrinth where they no longer produce abnormal responses. Most subjects with these conditions can be treated successfully by canalith repositioning maneuvers, including variations thereof, collectively known as particle repositioning maneuvers, which are designed to cause migration of aberrant particles to an area of the labyrinth where they no longer affect the dynamics of the semicircular canal.

These repositioning maneuvers are typically carried out manually on a table with a high success rate in the less complicated cases. However, for the more complicated cases, optimal performance of these maneuvers requires ongoing, real time observation and analysis of nystagmus. The nystagmus pattern may rapidly change during the performance of maneuvers, sometimes indicating the need for a critical change in strategy in the middle of a maneuvering sequence. In addition, and as mentioned above, the nystagmus patterns that subjects may display in response to maneuvers may be rapidly changing and complex, yet immediate interpretation is often required, and this requirement becomes more acute when the need for a change in strategy is indicated (e.g. a conversion of the causative particles from the posterior to the horizontal canal, or the development of a jamming of the particles). Very challenging, there is the need for the operator, during an entire sequence of maneuvers, to envision the 3-D orientation, with respect to space and gravity, of the semicircular canals inside the head, as well as the apparent position of the particles within those canals. This multi-level observation requirement is quite difficult because of the constant changing orientation in space of the subject during maneuvers. As will be seen, the present invention confidently addresses and solves these problems.

Thus, for optimum positional testing and particle repositioning strategy, the present invention features a head-stabilized 3-D orientation and tracking capability for generating data simultaneously regarding (a) the actual orientation, relative to space and gravity, of the semicircular canals of a subject, as well as (b) the angular acceleration being acutely imparted to the semicircular canals. Information regarding linear acceleration, possibly along with additional information regarding spatial inclination (derived from an appropriately employed inclinometer, or plural inclinometers) may be made available for use in this setting in accordance with the structure and practice of the present invention. Such data, fed to a watchful, and operatively and properly algorithmed computer, is displayed to the operator in a form that projects the actual orientation of the semicircular canals within a subject's head to a graphic user interface (GUI) image of the semicircular canals. This image is presented in a simulated environment that makes the orientation of gravity evident.

One related and very important novel contribution of the present invention is its demonstrable ability, on-the-fly, so to speak, to distinguish even very subtly existent pathological (abnormal) from physiological (normal) nystagmus events. This is extremely valuable to the clinician during testing or treatment, because of the fact that the nystagmus being observed in response to head maneuvers often contains components of both pathological and physiologic nystagmus. It is clearly advantageous to be able to observe and analyze just the pathological nystagmus without contamination by physiological nystagmus. Positional stability of sensors and stimulators in accordance with practice of the present invention leads significantly to the reliable ability to accomplish this differentiation.

Physiological nystagmus is mainly induced by angular acceleration of the head, with the slow phase of nystagmatic eye rotation occurring in the same plane as, but in the opposite direction from, head movement. This is a normal response reflex. Thus, by monitoring angular acceleration in addition to linear acceleration, while also monitoring, simultaneously, eye movement, and by doing all of this under conditions wherein the relevant monitoring sensors are firmly positionally stabilized relative both to one another, and to a patient's head, the present invention can effectively distinguish between those components of nystagmus that are physiological and those which are pathological in origin.

Further describing, in relation to this aspect of background information, certain relevant and important characteristics of the present invention, during a system calibration phase, the system of the invention determines the gain of the physiologically evoked nystagmus in each plane and direction. From this, it determines, in near real time, the slow phase component of physiologic nystagmus that would occur with each head movement, and then, during actual testing, removes its contribution to the total computer-generated information readout, thus leaving only the pathological nystagmus in the readout information.

Elaborating a bit on this above, brief summary outline, these pathological and physiological components may occur simultaneously, with each component contributing to the resultant nystagmus, and with the resultant nystagmus thus being made up of the vector sum of the planes, directions and velocities of the simultaneously occurring slow phase components. The slow phase vector for the physiological component is then subtracted from the slow phase vector of the presenting nystagmus, allowing a clinician to view just the purely pathological nystagmus for immediate use in diagnosis and in carrying out repositioning maneuvers. Understanding the investigative importance of performing this vector subtraction, and given the just presented outline describing the relevant data components requiring such subtractive processing, those skilled in the art will be readily equipped to implement an appropriate, computer-based algorithmic approach to accomplishing this.

Practice of the present invention in relation to the field of vestibular disorders, further accommodates the involvement of additional stimuli, such as the modification of air pressure experienced by the ears, oscillation of the skull, electrical stimulation, acoustic stimulation, etc., or any combination thereof, which may create pathologic nystagmus that can be analyzed to assist in the diagnosis and treatment of vestibular disorders.

In general terms, and broadly speaking from one structural point of view, the present invention can be characterized as including an assembly of mechanical, electronic and software components linked to positionally-stabilized, subject-head-worn apparatus, whereby, with a subject (person) oriented in, or moved through, certain positions, that subject may be presented with vestibular-relevant stimuli, such as visual images, sound and pressure change in the ears, head vibration, and therapeutic or diagnostic fluid flow into (and eventually out from) the middle or external ear, and simultaneously observed by both a computer and a human attendant for reflex eye movement, postural responses and spatial orientation as tracked with inertial and other positionally stabilized sensors, and/or by observation of subjective responses. Plural-parameter data, regarding simultaneous positional or other stimuli, and responses thereto, is integrated and analyzed electronically and displayed in an easily understandable form which includes vector analysis (above mentioned) of nystagmus, identification of the originating semicircular canals, and guidance for further tests and treatment. From a methodologic point of view, the invention can be characterized broadly as involving appropriate steps to implement this just-outlined structural view of the invention.

The invention also encompasses the physical characteristics of certain new, head-attachable structures, or devices, which play roles in the delivering of certain ear stimuli relevant to vestibular-disorder diagnoses and treatments, as well as to certain related new procedures.

As will also become apparent, the present invention opens a door to the assembly and use of a very innovative, computer-based, "expert-guided" system. Very specifically it enables the implementation of a feedback-endowed system, wherein a subject wearing device-stabilized (sensors and stimuli deliverers) headgear may be communicatively connected (tethered or "wire-free") to a computer armed with "expert"-trained algorithm structure which has been "taught" by highly skilled and experienced medical personnel to understand, in a broad spectrum, the significances of observable subject responses to matters such as spatial positions, maneuvers, delivered stimuli, and so on. This computer will be able to react to these observable phenomena with feedback-based information that can do a variety of things, such as (a) inform an attending "medical" operator of the system just what to do next with respect to a diagnostic and/or treatment step to perform with the subject, (b) modify the character, nature, etc., of various stimuli being delivered, or to be delivered, to the subject via the head-worn, device-bearing gear, (c) implement and/or modify the delivery of a liquid substance, such as a treatment and/or stimulation drug, to the subject's ear, or ears, and other things which will come to the minds of those skilled in the art. (One should note that the terms stimulus and stimuli are used herein to refer to all forms of "deliveries" including liquid deliveries for either diagnostic or treatment purposes, to a subject via the stabilized headgear of this invention.).

The invention thus effectively makes possible, anywhere in the world, the functional availability, to subjects suffering from vestibular disorders, of the world's most highly skilled vestibular-disorder experts. By the use of appropriate telemetry, all of this advantage can be invoked via "remote control". The following summary statements non-exclusively illustrate these "expert-system" possibilities.

Headgear for positional ontological vertigo (diagnosis and treatment) with goggles, inclinometers and accelerometers is employed. A subject is fitted with the headgear of the invention, and is placed on a table lying down. The attending system user (typically a physician) starts a maneuver protocol on the computer, which guides the physician's movements of the subject's head while simultaneously monitoring eye and head movements and analyzing associated pathophysiological nystagmus and head position, for the purposes of diagnosis and treatment assessment and maneuver adjustments where applicable.

Headgear for stimulus-evoked ontological vertigo with goggles, inclinometers, accelerometers, sound, pressure, vibration, light, etc., is employed. A subject is fitted with the headgear of the invention (with ear inserts), and is placed in a chair, or positioned standing up. The attending system user (again typically a physician) starts a stimulus protocol on the computer, which generates a set of ear and/or head stimuli, whose resulting subject eye and head movement responses are simultaneously monitored and analyzed for pathophysiological nystagmus and head position, all for the purposes of diagnosis and additional stimulus-response protocols where applicable.

Headgear for intratympanic drug delivery with goggles, inclinometers, accelerometers and fluid flow system is used. A subject is fitted with the headgear of the invention (with ear catheters), and is placed on a table lying down, or in a chair. The attending system user starts a fluid flow protocol (e.g., drug delivery) on the computer, which provides intratympanic fluid exchange, while simultaneously monitoring subject eye and head movement responses, and analyzing for pathophysiological nystagmus and head position, for the purposes of treatment assessment and fluid flow adjustments where applicable. In this kind of procedure, which should be distinguished from a caloric-stimulus procedure, a local anesthetic such as lidocaine might be employed as a perfusate tag.

These and other features and advantages of the invention will become now more fully apparent as the description which here follows is read in conjunction with the accompanying drawings

DESCRIPTION OF THE DRAWINGS

FIG. 8-10, inclusive, illustrate the structure and use of a trocar device, also referred to herein as fluid-flow structure, constructed and employable in accordance with a preferred embodiment of, and manner of practicing, the present invention.

DETAILED DESCRIPTION OF THE INVENTION

Figure 1:
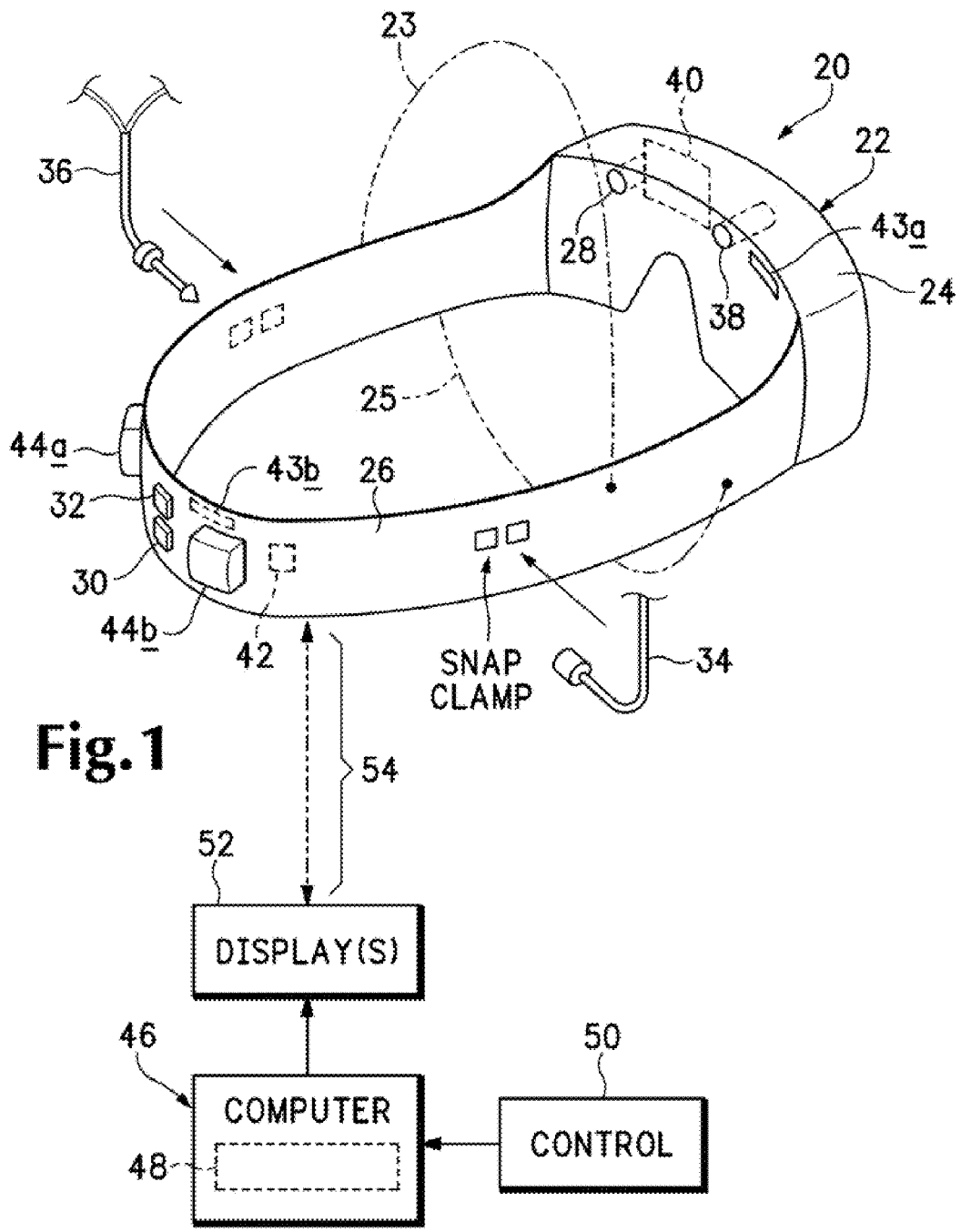
FIG. 1 is a somewhat simplified, block-schematic view illustrative of one form of the apparatus (also referred to sometimes as a system) and methodology of the present invention.

As has been mentioned above, the present invention, from a structural point of view, takes the form generally of apparatus for assisting in the computer-aided, substantially real-time diagnoses and treatments of vestibular disorders. That apparatus features head-wearable frame structure that is adapted for wearing on a subject's head in a condition of relative positional stability. The invention further features, in association with that frame structure, at least a pair of what are referred to as vestibular-parameter, data-parameter devices that are selectively anchorable to the frame structure in conditions of relative positional stability, both with respect to the frame structure, and with respect to each other. Each of these devices, in accordance with the invention, is adapted to engage in at least one of the activities which include (a) delivering to, and (b) receiving from, a subject's head vestibular-relevant parameter data. Appropriate communication structure connects these devices operatively to appropriate computing structure (a suitably "algorithmed" digital computer). This communication structure, in relation to its use intermediate the mentioned devices, is adapted to accommodate tasks including (a) communicating parameter data to, and (b) communicating parameter data from, those devices that are anchored to the head-wearable frame structure.

Of key importance in the implementation, practice and structure of the invention are that the wearable frame structure be securable on a subject's head in a manner whereby it effectively moves as a unit with the head, i.e., without any appreciable relative motion between the head and the frame structure, and that the particular plural devices which are employed to produce correlative data that is useful in the diagnosis and treatment of vestibular disorders, when anchored to the frame structure, be so anchored in manners that they are permitted no appreciable relative motion both with respect to the frame structure, and with respect to one another. With these non-relative-motion conditions met, and in accordance with practice of this invention, correlation between various types of data derived from a subject, and various types of stimuli delivered to a subject for the purpose of developing such receivable data, are tightly linked in manners which produce extremely useful and informative data to a physician, clinician, or other qualified user of the system and methodology of the invention.

In the description which now follows, two different specific types of head-wearable frame structures are illustrated and generally described, and materials employable therein are suggested, but it should be recognized that the invention is not dependent in any way upon any specific frame-structure configuration or materials. What is important with respect to such a frame structure is that is be securable to a person's head in a wearing condition wherein it will effectively move as a unit with the wearer's head during practice of the invention. Inasmuch as the integument overlying the head is compliant tangentially, the head-mounted apparatus is further stabilized for some uses by placing stabilizing inserts into the external ear canals. Further, a relatively wide range of devices, both sensor and stimuli delivery devices, is illustrated herein, which devices are considered very relevant to the examination of vestibular disorders. This list given herein is not intended to be exhaustive, and it is recognized that other kinds of devices, which may be useful with respect to examining and treating of vestibular disorders, may be employed.

Additionally, and as has been mentioned, it is important that sensors and stimulators (devices) that are to be anchored (for use) to the head-wearable frame structure of the invention be so anchorable in manners whereby they do not move relative to that frame structure, and thus do not move relative to one another when anchored to that structure; but this does not necessitate any particular style or kind of anchoring structure. Preferably, such anchoring structure allows for selectable and removable anchoring of such devices, but whether or not such removability is in fact enabled, no specific kind of anchoring structure forms any part of the present invention. Rather, those skilled in the art will recognize that there are many different types of suitable anchoring modalities, removable or not, which may be employed. Accordingly, no specific anchoring structure to accomplish this task is detailed herein.

The present invention thus offers as a contribution to the art, among other things, the important recognition that the two mentioned levels of positional stabilization play very significant roles in the acquisition of tightly correlated relevant data which can, far more readily than with respect to similar data collected from past practices, arm the professional observer with especially improved, useful, accurate and insightful information regarding analysis and treatment of vestibular disorders, with respect to which even modest amounts of otherwise expectable poor correlation between data can significantly challenge effective analysis and treatment.

Figure 2:
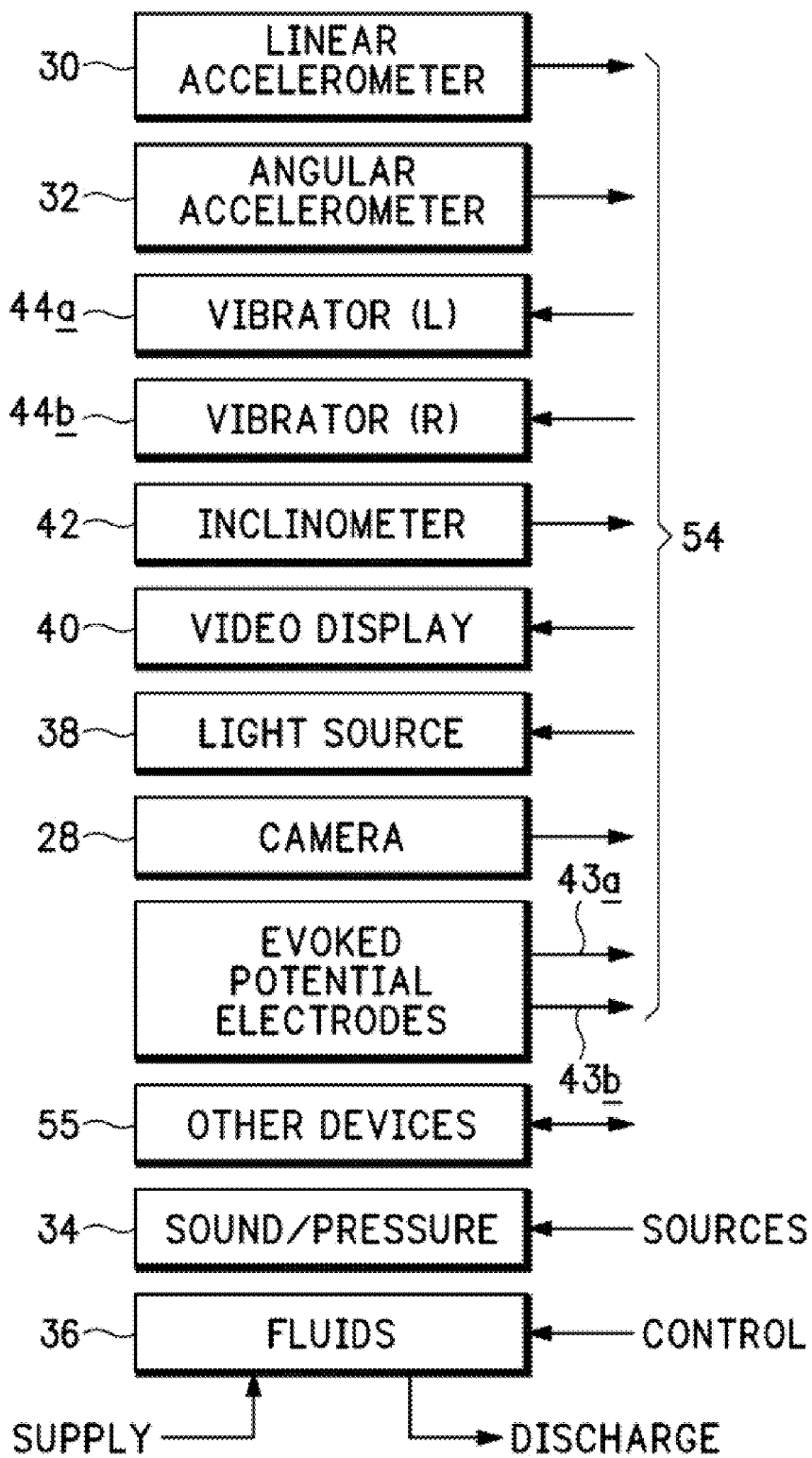
FIG. 2 is a block/schematic view further illustrating the structural and methodological elements of the invention generally shown in FIG. 1.

Turning now to the drawings, and beginning first with reference to FIGS. 1 and 2, indicated generally at 20 in FIG. 1 is one form, and collection, of apparatus constructed and useable in accordance with a preferred implementation of, and manner of practicing, in a best-known mode, the present invention. Apparatus 20, as illustrated in FIG. 1, takes the form of a goggle-like frame structure 22 which includes an eye-bridging housing structure, or housing 24, and a head-wrap band 26 which extends from housing 24 in a loop that enables the frame structure to be secured appropriately, in a goggle-wearing fashion, to and around a human subject's head. Band 26 is preferably length-adjustable (in any suitable manner which is not specifically illustrated herein) to enable appropriate and comfortable tightening around the head, is preferably formed of a relatively configurationally stable plastic material, such as a medical-grade polycarbonate material, and may have all, or a portion, of its inner surface equipped appropriately, if so desired, with any suitable high-frictioning material, such as silicone rubber. Whether or not such a frictioning material is employed is completely a matter of choice, it only being important, in accordance with the structure and practice of this invention, that when this frame structure is "installed" in a secured condition on a subject's head, it will effectively occupy a condition thereon of substantially complete stability with respect to no relative motion being permitted between the frame structure and the head under normal subject head-motion conditions.

While frame structure 22 is shown as simply involving the two components specifically illustrated and mentioned, it can clearly be modified, if so desired, with other stabilization features, such as an additional strap which might have opposite ends joined to band 26 to extend adjustably and tightenably over the crown of the head, as suggested by dash-dot line 23. It might further include, also if so desired, additional stabilization provided by something in the nature of a conventional, tightenable and adjustable under-the-chin strap, as suggested by dash-dot line 25, and by the previously mentioned ear canal insert.

As has been mentioned earlier herein, practice of the present invention contemplates the selective simultaneous use of plural (at least two at a given time) devices, appropriately anchored to frame structure 22 for the purpose of either collecting data from a subject relative to vestibular behavior (sensors), and/or delivering stimuli to a subject (stimuli deliverers). A representative (but non-exhaustive) list of such devices is now presented, and each of these different kinds of devices is illustrated just very simply and schematically in FIG. 1 in place at a representative selected location on structure 22. Thus, the illustrated devices include a small infrared video camera, or electronic video-image collecting device, 28 which is suitably positioned inside housing 24, a three-axis linear accelerometer 30, a three-axis angular accelerometer 32, a combined sound deliverer and air-pressure modifier 34 (stimuli deliverers), a device 36, referred to herein as fluid-flow structure, for delivering selected fluids/liquids to the ear (also a stimulus deliverer), a suitable, selected light source, or light-emitting structure, 38 which is also mounted inside of housing 24, a small video screen, or visual image-presenting structure, 40 which is disposed within housing 24, an inclinometer 42, a pair of spaced evoked-potential electrodes 43a, 43b, and two (left and right) vibration-generating structures, or vibrators, 44a, 44b, respectively (also referred to as stimuli deliverers).

It should be understood that, with respect to the very simplified illustrations presented in FIG. 1 for these several devices, and with regard to the specific locations illustrated for them, the selections of the devices per se, and the "best" locations thereof with respect to their points of stabilized attachment to frame structure 22, are completely matters of selection and choice. Preferably, of course, the video camera device, the video screen device, and the light source device are all contained within housing 24, and preferably they are disposed in such a fashion that they principally address attention to a selected one of a subject's eyes when the frame structure is mounted in place including these devices. Substantially always present, in addition to at least one other device on frame structure 22, is camera device 28 which feeds a data stream that allows an operator practicing with the invention to observe a wearer's nystagmus behavior.

The exact dispositions which are chosen for the mentioned accelerometers, and for the mentioned inclinometer, are, as suggested above, purely matters of user choice.

While the two vibrators 44a, 44b are preferably disposed as left and right vibrators which are independently operable to deliver selected vibrations to a subject's head, and while these two vibrators are shown positioned near what will be the rear side of band 26 when frame structure 22 is in place on a subject's head, one might selectively choose to employ only a single vibrator, or to position plural vibrators somewhat differently.

With further regard to the use of vibrators, it may be desirable to create a suitable, effective isolation and ignoring of the physical motion disturbances which operation of a vibrator might introduce to other devices carried by the headgear of the invention. Conventional mechanical and/or electronic approaches may be used for this purpose, if desired. With appropriate steps taken to cause other devices carried by the frame structure to ignore vibrational motions undergone by such vibrators, these vibrators are considered, in accordance with the invention, to be "positionally stabilized". It should also be noted here that one manner of using plural vibrators, uniquely enabled by the present invention, is in what can be thought of as a selectively "out-of-phase" manner, whereby "focal points" of vibration can be established at selected regions inside a subject's head.

As was mentioned briefly earlier, the vibrators can by positioned and the phase of their oscillation varied so as to target a particular location at which the waves of oscillation converge to form a node of increased vibration. For this, an array of several vibrators can be positioned and phase-adjusted to accentuate this effect.

With respect to device 34 which herein takes the form of a combined sound deliverer and air-pressure modifier, just one of these devices is shown, and only fragmentarily so in FIG. 1, close to what is the near side of band 26 in this figure. It should be understood, of course, that two of these devices might be employed if it were desired to furnish one or both of such stimuli (sound, air-pressure modification) to both ears, with such two devices then employed appropriately anchored to opposite lateral sides of band 26. Also, it is not necessary that a device 34 have a bimodal capability. In other words, one could choose to employ independent sound delivering and air-pressure modifying devices.

Fragmentarily illustrated fluid-flow structure 36, only one of which is shown in FIG. 1, could be used in combination with a second such device on the opposite side of band 26, thus to deliver stimuli and/or treatment fluids (liquids) selectively to both ears if desired.

Further with respect to devices 34, 36, while these particular kinds of devices may take a number of different forms, certain preferred, specific constructions for these devices have been found to work especially well in the environment of the present invention, and these specific constructions are illustrated and described herein also, and are specifically discussed a bit later in this text.

Referring now to FIG. 2 along with FIG. 1, further incorporated into the arrangement and practice of the present invention are a computer, also referred to as computing structure, 46, which includes appropriate internal algorithm structure which is represented by a dashed block 48 in FIG. 1. Computer 46 is user controllable via an appropriate user controller represented by a block 50 in FIG. 1 which is labeled CONTROL. An appropriate monitor screen-display device 52 (or more than one such device, if desired) is coupled to computer 46 for presenting various visual output information to a user of the system. While only a single display device is thus specifically illustrated, it should be understood, as just above suggested, that plural display devices may be coupled to computer 46. It should also be mentioned that an appropriate display device might be directly connected to camera 28, if desired. A later herein presented description of a typical use of the invention specifically includes an illustration of this option.

Appropriately interconnecting computer 46 with whatever devices are employed in conjunction with headgear apparatus 20 is what is referred to herein as a communication structure 54. This structure is entirely conventional, and might either be a form of hard-wired structure, or a form of wireless communication structure, or some combination, for example, of the two of these things.

As can be seen with respect to FIG. 2, each one of the various several devices that have just been mentioned above in relation to FIG. 1 is represented in block form in FIG. 2. Single ended arrows extend to and from these block illustrations to represent, generally speaking, the direction of parameter data flow. The bracket presented centrally in FIG. 2 represents a selected communication structure 54 which extends between these block-represented devices and previously mentioned computer 46. One exception here is that the two arrows which are associated with combined sound and air-pressure deliverer 36, labeled SOURCE, represent appropriate sound, and/or air-pressure controlling, sources.

Included in FIG. 2 is a block 55 which is labeled OTHER DEVICES. Two dashed-line arrows, one pointing inwardly toward block 55, and one pointing outwardly from the block are associated with this block. Block 55 represents the recognition that various sensor and stimulator devices other than those specifically listed herein, such as a device for introducing galvanic stimulation, and a device for introducing caloric stimulation, may readily be employed if desired.

At the bottom of FIG. 2 there is a block which is labeled FLUIDS, and this represents a source and return reservoir of fluids supplied to and drawn away from, as appropriate, device 36 when that device is being employed as a fluid-flow structure. A single-headed arrow pointing into the right side of this block, labeled CONTROL, reflects a connection through the communication structure to computer 46, whereby this computer, monitoring nystagmus behavior in a subject, is enabled to control the delivery of fluids, for example, to one of a subject's ears via device 36.

In very general terms, when the apparatus and methodology of the present invention are to be employed with respect to a particular human subject, that subject is equipped with headgear apparatus like that illustrated in FIG. 1, which apparatus is then suitably communicatively coupled to a computer, such as computer 46, which is under user control by a user controller such as that represented by block 50. Computer 46 provides an appropriate output display on a monitor device, such as that shown at 52. With regard to a particular practice of the invention, the professional user (physician, clinician, etc.) of the invention selects the devices which are to be employed, one of which will nearly always be a video camera device, such as device 28, which watches subject eye movement. The user affixes the selected devices, to defined positions on and with respect to frame structure 22, which frame structure is then suitably secured in a fixed-worn condition on the user's head.

In accordance with important positional constraints that form parts of the contributions of the present invention, under the circumstances now created for use of the invention, the head-worn apparatus is effectively secured against the kinds of undesired relative motions which have been described earlier herein. Very specifically, the frame structure which supports the various stimuli and sensor devices that are to be employed is itself anchored securely against relative motion on the subject wearer's head, and the individual devices selected for use on the frame structure are anchored thereto against motion relative either to that frame structure or to one another.

A situation is then set whereby data acquired from a subject during a diagnostic and/or treatment procedure, and stimuli delivered to that subject, are sufficiently positionally locked relative to one another whereby an important correlation will exist in acquired data. Because of the positional stabilization conditions which are thus established, in accordance with practice of the invention, relationships between stimuli and subject responses, as well as relationships between maneuvers which are performed to reposition a subject during observation, and responses in association with those movements, are tightly correlated, and information is made available for computer processing, and for user observation and use, which can accurately pinpoint potential sources of vestibular disorders. By employing both linear and angular accelerometers, along with other related devices, such as an inclinometer, observable nystagmus activity, both physiologic and pathologic can readily be separated so that a user of the system can focus upon nystagmus behavior which is relevant to a desired diagnosis and/or treatment.

Figure 3:
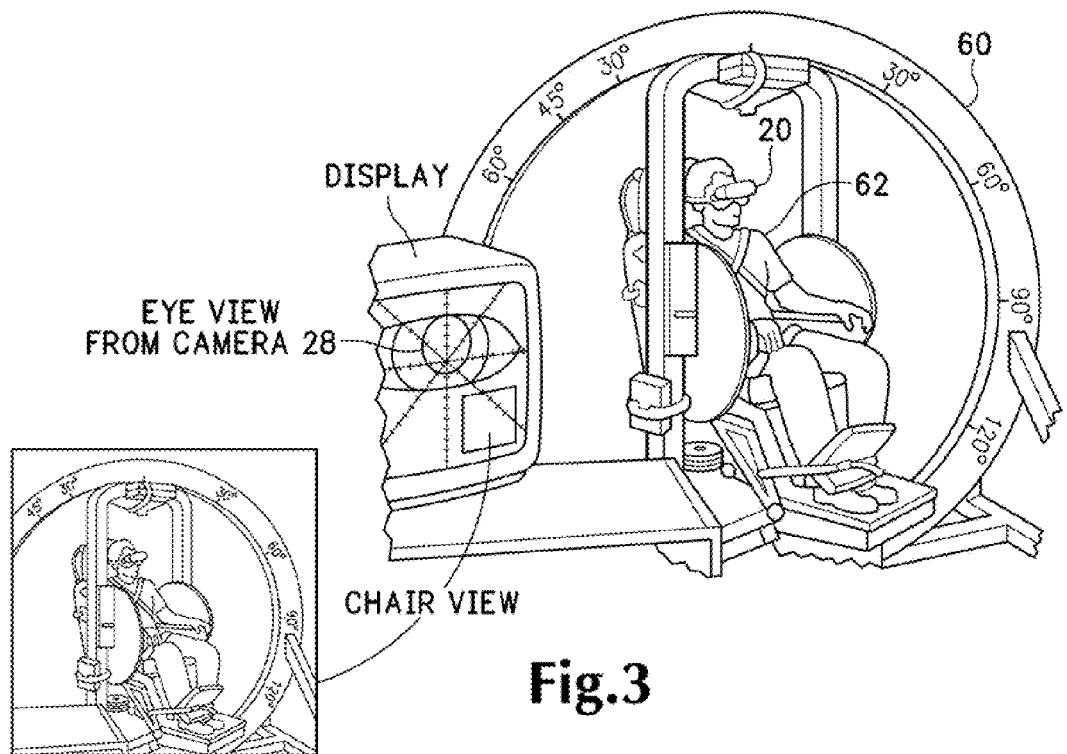
FIGS. 3 and 4 are fragmentary illustrations of a human subject supported in two different angular orientations in a positional maneuvering chair which may be employed to perform spatial maneuvering and positioning of the subject during a procedure employing the present invention. These two figures also show, fragmentarily, a representative video display screen which presents visually observable output information derived, among other things, from practice of the invention.
Figure 4:
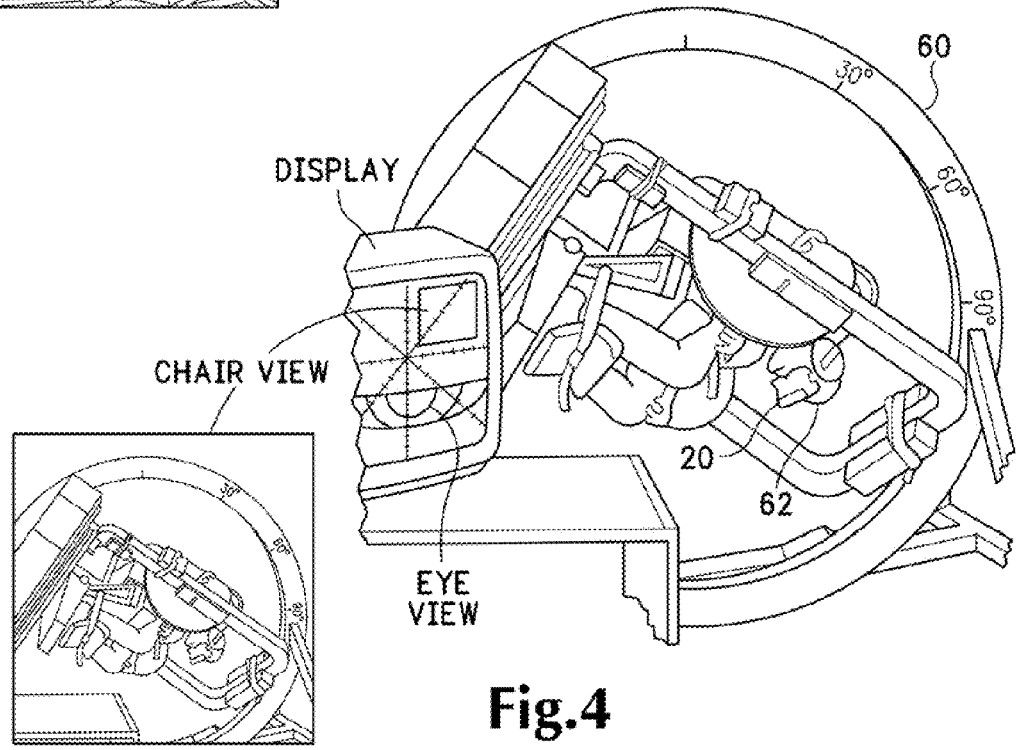
Figure 5:
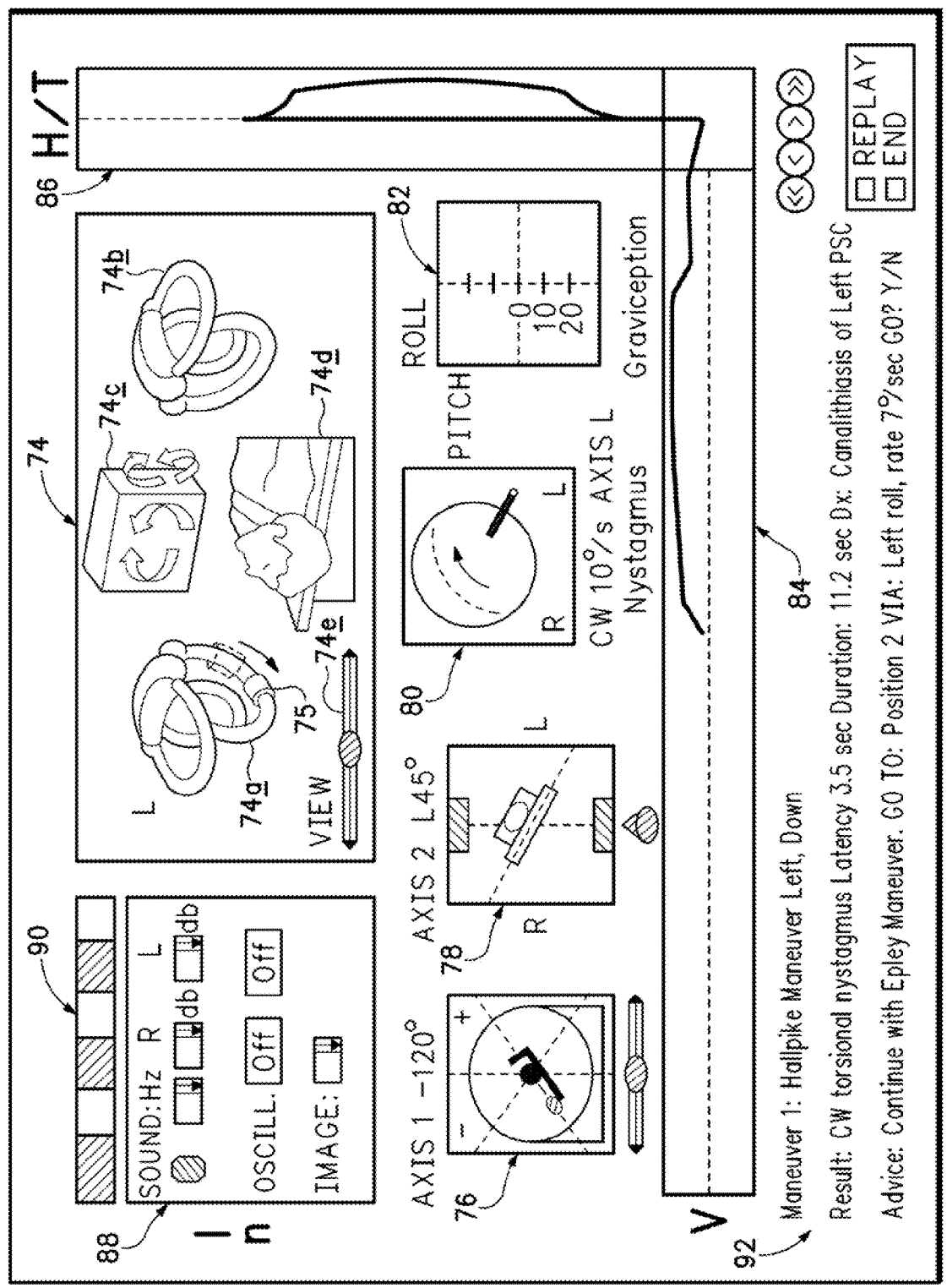
FIG. 5 is an illustration of a computer monitor display screen which is shown presenting various correlated graphic and pictorial imagery that represents a typical user-accessible display of information correlating data derived from headgear-worn apparatus stabilized in accordance with implementation and practice of the present invention.

Turning attention briefly now to FIGS. 3-5, inclusive, here one modality for using the system of the present invention is generally illustrated.

Very specifically, shown at 60 in FIGS. 3 and 4 is one form of a subject-support maneuvering chair which is mounted within a plural, articulated, motor-driven ring structure which can be operated, either under manual direction, or under computer control, essentially to position a subject in substantially any spatial plane of interest, and specifically with the subject's head oriented in any plane of choice. FIG. 3 shows device 60 orienting such a subject in one upright orientation, and FIG. 4 shows the same subject in a rotated and somewhat inverted, different orientation. In these two figures, the subject is shown generally at 62. Additionally, this subject is shown equipped with headgear apparatus 20.

Shown fragmentarily in FIGS. 3 and 4 in close proximity to device 60 is a display monitor 63 which is shown providing a user of the system with certain video imagery 64. This imagery pictures the subject's eye, derived via camera 28 (direct connection to monitor 63). Also displayed is a small image 66 picturing a view of the spatial orientation provided for subject 62 by chair 60. Such a view might be provided, for example, by a remote external video camera which is not part of the present invention.

In the representative arrangement now being described, computer 46 is appropriately connected to device 60 to exercise position and motion control over this device.

FIG. 5 illustrates a representative display of information which might be provided on a display-screen device, such as device 52. What is specifically shown in this figure is now described in conjunction with subject 62 and chair device 60. Thus, in FIG. 5, one sees presented on the illustrated display screen a variety of different pieces of information that may be derived from and in relation to sensors and stimulators anchored to head-worn apparatus, such as apparatus 20.

Here in FIG. 5 there are, generally speaking, nine different pictured graphical pictorial image areas which are shown generally at 74, 76, 78, 80, 82, 84, 86, 88, 90. A text-presentation area 92 is also provided. While these several specific image site areas have been chosen for illustration herein, it should be appreciated, and it will become apparent, that a greater or lesser number of site areas, and the specific internal contents of each such site area, can be changed and varied within the scope of the invention, to suit different specific applications. No matter what in fact are the contents presented on a display screen, such as that shown in FIG. 5, these contents include an appropriate presentation, to a user of the invention, of intuitively and easily grasped visual and pictorial information which correlates different components of data that are presented and gathered by computer 46 during a diagnostic investigation and/or treatment procedure.

Very specifically, it is a feature of the present invention to provide such visually correlative data which will give a system user an intuitive and quick grasp of the specific vestibular behavioral situation and anatomical spatial orientation which is under way in real time, and at any given moment, with respect to a subject whose vestibular system is being explored and/or treated. Contents which are pictured as being displayed on the screen in FIG. 5 demonstrate this important capability and offering of the present system.

Included within image site area 74, are five pictorial/abstract icon-like images 74a, 74b, 74c, 74d, 74e which represent different things, as will now be described. Each of these images takes the form herein preferably of a user-accessible interactive control icon which will allow a user, through manipulation of a control device, such as a mouse, and the cursor driven by the mouse, to perform various manipulations of the spatial orientation of a subject, such as subject 62. Icons 74a, 74b, are pictorial, virtual, surrogate, anatomical representatives of the right-side and left-side semi-circular canal structures, respectively, in subject 62, positioned relative to one another, and pictured with a spatial orientation which is intended to match very closely the actual orientations in space of the subject's actual semi-circular canal structures. The icon images which are presented at 74a, 74b are rendered with appropriate three-dimensional cues on a two-dimensional screen, whereby they quickly give a viewer a clear understanding of the orientations and dispositions of these canal structures.

By placing, for example, a mouse-controlled cursor on either one of these representative icons, and by maneuvering the cursor through appropriate mouse manipulation, the system user can call for a fairly exact repositioning at any time of an actual semicircular canal structure in the subject. Such manipulation will result in a control signal being sent by computer 46 to the motors that control operation of device 60, so as to orient the subject, whereby the accelerometers that are responsive to the subject's head position directly produce an indication that the subject's head has been repositioned. The data-streams which control the spatial representations of icon images 74a, 74b come to the computer from the headgear sensors via communication structure 54, as shown in FIG. 1. This collection of data essentially represents what might be thought of as absolute three-dimensional spatial-orientation data regarding the then subject's head position and orientation.

A small visual element, shown in image site 74 at 75, is appropriately creatable under computer control to represent the positions and flows of various particles and activities which may be playing a role in a vestibular problem that is being experienced by the subject. Under appropriate commands, not specifically illustrated herein, a system user can call for the presentation of this small visual element, with positioning of the element along the run, for example, of a given semicircular canal, being determined through computer calculation based at least in part upon data coming from the headgear accelerometers, and other data components that are received during a test and/or treatment procedure. The exact manner of creating such a small visual element and placing it appropriately along one of the canals is completely a matter of user and system-designer choice, and can be implemented in a number of different ways, none of which forms any special part of the present invention. Further, algorithmic information contained within computer 46 which permits representation and control through icon visual elements 74a, 74b is well within the skill levels of those generally skilled in the art of writing computer programs, and is not considered to be any part of the present invention. Suffice it to say that there are many different approaches which one can use to implement such moveable and control iconry.

Visual icon elements 74c, 74d relate in slightly different ways to the actual orientation in space of the elements in manipulation chair 60. Both, of course, are virtual representations, with icon 74c being quite abstract in nature and icon 74d being somewhat pictorially representative of a subject within the chair in device 60 as pictured herein. Both of these icons are user-interactive icons which can be manipulated through mouse and cursor control to effect re-positioning, and appropriate rotational positional motion, of the interconnected structures in device 60. These icon elements appear to rotate within image site 74 when structure within device 60 moves from one condition to another. A user, by manipulating either one of these two icons through mouse and cursor control, can thus cause the computer to send appropriate control signals to operate the motors (not shown) in device 60. The actual spatial conditions which are thus achieved and represented by the positions of the icons on screen pictured in FIG. 5 are synchronized through one or more data-streams received by computer 46 over communication structure 54 from appropriate sensors directly attached to components in device 60.

Icon component 74e is a virtual representation of a control slider which, as pictured in FIG. 5, is permitted generally horizontal adjustment to the left and to the right under mouse and cursor control, to shift the point of view, for example, of an external camera structure looking at device 60. Appropriate manipulation of the slider knob in this icon to the left and to the right will cause the surrogate pictorial representation of a subject in the maneuvering device chair to rotate within image site 74 so as to reflect a selected new point of view.

It should be understood that, no matter whether a position and spatial orientation adjustment occurs through manipulation of the icon components within image site 74a, controlling the motion of a positioning device, or through providing guidance for an operator to maneuver the subject directly, any motion and repositioning taking place with respect to the components in device 60, and with respect to the actual orientation of the head of subject 62, will be communicated through computer 46 to the representations of the respective iconry within image site 74. In other words, these icon images will follow whatever positional adjustments and establishments take place.

Image sites 76, 78 contain appropriate iconry which represents two different axial point of views relating to motion or rotation axes that are furnished within maneuvering device 60. Image site 76 pictures a side view, so-to-speak, and image site 78 a top axial view. A slider control which is included at the base of image site 76, and a rotary virtual knob control which appears at the base of image site 78, is/are manipulable through mouse and cursor control by a user, and through the agency of operation of computer 46, directly to manipulate device-60 motion in selected angular manners. The specific central icon imagery which is presented at these two sites adjusts in pictorial condition to reflect actual conditions, and thus to reflect motion between one condition and another condition of, for example, the chair that supports subject 62. Numeric reports with respect to angular disposition about different axes can readily be provided in association with these image sites, and such information is generally pictured numerically at the upper sides of image sites 76, 78 in FIG. 5.

Manipulation of the chair structure through controls provided via iconry in sites 76. 78 will be reflected by imagery positional changes of the icons that are associated with such conditions as pictured in image site 74.

One of the appropriate algorithmic components of the algorithm structure contained within computer 46 observes various data components supplied to the computer from structure 20 to assess current nystagmus activity in subject 62. This activity, which can be thought of as being involuntary subject activity, and which can depend, in certain instances, upon the spatial orientation, upon the angular motion or acceleration, and/or upon various disease processes, of and relating to subject 62, is processed by the computer, and presented in graphical and visual form within image site 80 in FIG. 5.

Image site 80 depicts the momentary profile of the fast phase of the ongoing nystagmus, as determined by either digital nystagmus analysis or input from the observer. Inasmuch as any movement of the eyeball during a moment in time involves a rotation in a certain plane, and thus about a certain axis that is perpendicular to that plane, it is possible to depict any such movement by designating the coordinates of the axis and the direction of angular movement about that axis. Thus, the sphere (the circle) depicted in site 80 represents the eyeball as viewed from the frontal plane, the projecting pole represents an axis, and the curved dashed line represents the plane of rotation of the equator. The curved arrow points out the direction of rotation about the mentioned axis.

With what is shown in image site 80 presented along with what are shown in image sites 74, 76, 78 herein, it will be very apparent how the system and methodology of this invention present, graphically and visually to an observer, intuitive and easily graspable correlative data that links actual spatial orientation of a subject and of a subject's head to a subject's involuntarily created condition of nystagmus activity. This correlative-data presentation provides a powerful tool in real time for a user of the system to gather and form an assessment regarding the efficacy of treatment, if that is what is taking place, and/or to reach a diagnosis relating to vestibular problematic behavior.

Image site 82 relates to another data stream, but here one which is created voluntarily on invitation or command from the system user directed to the subject to introduce an input, for example, which reflects the subject's perception of the gravitational vector. This information can be compared for analysis purposes with non-subjective gravity information arriving from an inclinometer carried on apparatus 20.

Recognizing now the presence in the screen display presented in FIG. 5 of such a rich supply of spatial orientation and subject perception (both voluntary and involuntary) regarding various components of vestibular activity, it should be very apparent how the system presents to a user an extensive and quite easily grasped all-over "image" of the behavior of the subject's vestibular system, as such behavior is dictated by specific orientations in space, and/or by specific motions in space between different orientations.

The two, divergent time-based curves or graphs which are represented in image areas 84, 86 display the recent nystagmus slow phase velocity data in a scrolling manner that allows for improved review and analysis through a greater insight into the present and previous responses. This can be provided by virtue of a divergent scrolling design that is highly intuitive as follows: first, the deflections of the horizontal and vertical tracings of eye movement are converted into their respective slow phase velocity components; second, the intensity of these components is indicted by the extent of their deviation from the median line of the graph; third, the direction of their deviation is determined by the actual direction of the fast phase of the nystagmus, which is the direction by which nystagmus direction is conventionally indicated; and fourth, these tracings are oriented to scroll in two diverging directions—horizontally from right to left, and vertically upward.

Tracings scrolling along the horizontal line represent the vertical component of the slow phase, so that its deflections will be vertically oriented, and an upward deflection represents an upward-directed slow phase, and vice versa. Tracings scrolling along the vertical line represent the horizontal component of the slow phase, so that its deflections will be horizontally oriented, and a rightward deflection represents an rightward-directed slow phase, and vice versa. Finally, this scrolling keeps its origin point at one general location, but the resultant tracing continues to scroll horizontally across or vertically up the page, so that the time line of recent activity will become apparent. A cursor across the median line of each graph can be moved to a particular point and a cursor on the other graph will be automatically moved to the same point in time. The operator can thus move to a previous point in time to review a particular sequence, with the remainder on the graphic display playing out the sequence.

Also, as an example, the present design can provide for the slow phase velocity of the torsional component to be displayed with the horizontal channel tracing, but in a different color, denoting the left or right angular direction of the superior pole of the fast phase.

Actual angular acceleration data from the angular acceleration sensors can also be depicted in the display, placed as a separate tracing (distinguished by color or character, in virtual real-time adjacent to the slow-phase velocity (SPV) tracing, and oriented in their respective vertical and horizontal channels of the SPV display. Thus, the expected normal positioning-induced nystagmus, and after-nystagmus, from angular acceleration of the head can be correlated with the actual nystagmus tracing, and will be less likely confused with particle-induced nystagmus. Also, the timing, direction and velocity of transition and test moves will be more evident.

In FIG. 5, the image area marked 88 is presented as an illustration of how one form of perception denormalization, and namely one involving the introduction of sound to one or more of the users ears through the stabilized apparatus of the invention can be viewed and controlled, and observed by computer 46. Thus, within image area 88 in FIG. 5, one can see that there are controls provided relative to sound denormalization involving selection under computer control of the frequency content of introduced sound, and of the relative volumes of this sound denormalization activity as presented to the left and right ears in a subject. Various on and off controls are provided to afford flexibility in sound application.

It will be understood of course, that essentially all information furnished visually on a display such as that pictured in FIG. 5, is based upon accurately correlated data derived for the various activities of the positionally stabilized sensors and stimulators chosen for use in apparatus 20.

Figure 6:
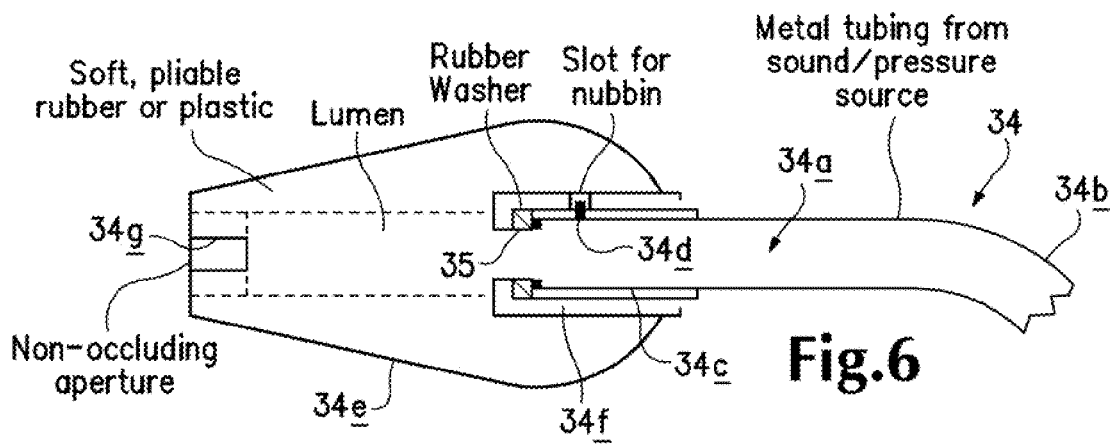
FIG. 6 (fragmentary) and FIG. 7 (derived from FIG. 6) show two different views in simplified form of a combined sound deliverer and air-pressure modifier device which is employable in accordance with a preferred embodiment of, and manner of practicing, the present invention.
Figure 7:
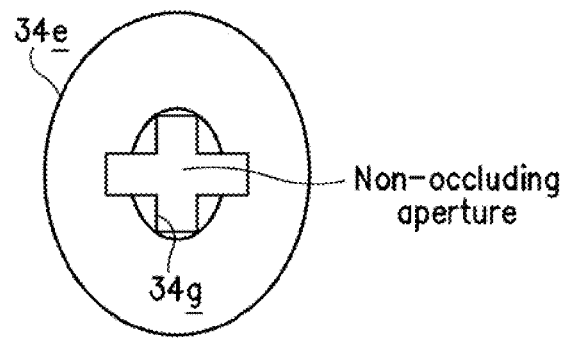

As was mentioned earlier, I have found that there are certain specific structures for devices 34, 36 which work especially well in the headgear-apparatus setting of the present invention. FIG. 6 and 7 illustrate a preferred construction for a combined sound deliverer and air-pressure modifier device, such as device 34. FIG. 7 is taken generally along the line 7-7 shown in FIG. 6.

Combined device 34 includes an elongate tubular body structure 34a, which may be furnished with a generally right angle bend as is shown at 34b, and which may be made of a relatively rigid plastic material, with this tubular body including what is referred to herein as a delivery end 34c inwardly from which there is provided an outwardly projecting nubbin 34d. Fitted removeably and replaceably on this outer body end is a soft and pliable, typically rubber-like oblong and tapered bulb 34e which is fitted with a mounting structure 34f that enables removable, nubbin-locked positioning of the bulb on body end 34c. Bulb includes an outer exposed end possessing a cross-shaped non-occluding fluid-passage aperture 34g. A washer 35 provides sealing engagement between bulb 34e and body end 34c.

The non-illustrated end of tubular body 34a, during use of this device, is suitably coupled to a source of selected sound, or to a source which enables plus and minus varying of air-pressure under circumstances with body end 34c and bulb 34e suitably inserted into a subject's ear. The soft and pliable nature of bulb 34e, when engaged with ear tissue, produces effectively a fluid tight seal with this tissue which enables the development of pressures both above and below atmospheric pressure. It also provides a relatively good acoustical seal against the introduction of extraneous noise to the ear under circumstances where it is intended that a specific sound be delivered to the ear or ears.

Figure 8:
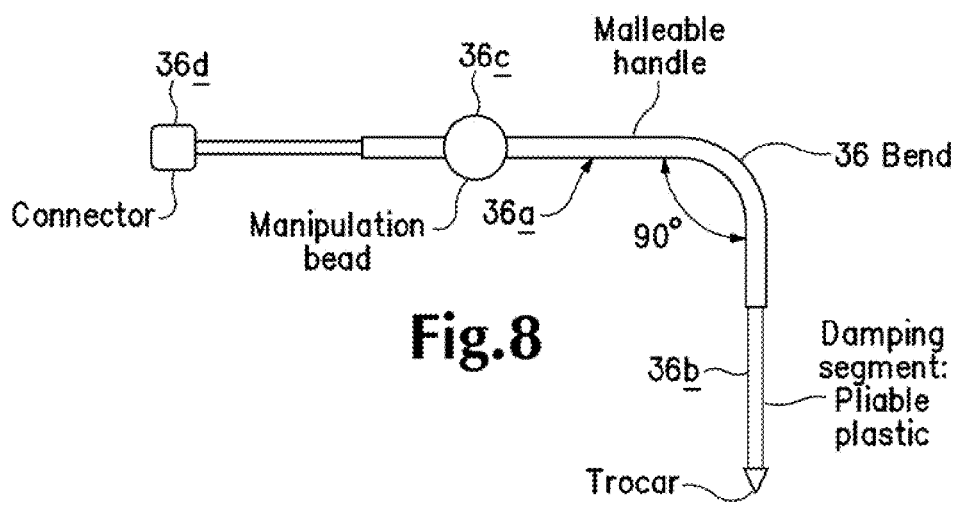

FIG. 8-10, inclusive, illustrate a preferred embodiment and manner of utilizing a structure such as fluid-flow structure 36. In general terms, this preferred structure includes an elongate tubular and malleable body 36a which is either formed with, or provided with, a removably attachable, outer trocar end 36b having the evident sharpened structure which permits selective piercing and penetration of the tympanic membrane as is illustrated in FIG. 9. Leading to the trocar is a compliant, easily bendable tube designed to absorb noise and shock imparted inadvertently from the body portion. Malleability in the body enables changeable formation of the bend in the body to accommodate appropriate positioning of trocar end 36b when device 36 is anchored to frame structure 22.

Suitably provided on body 36a, at a location which is somewhat distant from the trocar equipped end of the device, is an enlargement which provides what is referred to herein as a manipulation bead 36c that permits digital manipulation conveniently of this device during insertion, and during stabilization while readying and applying fixation molding material, or other fixating material, such as is illustrated in FIGS. 9 and 10. Just on the opposite side of bead 34c is an appropriate connector 36d which permits connection of one or more appropriately provided fluid lumens within body 36a to a suitable source and reservoir for delivery and return of fluid. For example, a delivery lumen might be connected to the source of a particular liquid drug which is intended to be delivered into the ear during a vestibular-examination procedure.

As can be seen in FIGS. 9 and 10, a generally illustrated procedure for use of device 36 is shown wherein the trocar end of the device, under the observation of a suitably placed viewing scope, is inserted through a slotted speculum into the ear to pierce the tympanic membrane. The slotted speculum is then removed, while still carefully stabilizing the trocar. Following this, and through any suitable device which can eject an appropriate stabilizing and sealing material, the region around body 36a is encapsulated in a flowable and curable sealing substance of any suitable variety, thus to provide local stabilization between the position of the device and the immediately adjacent ear structure. Manipulation of the device during insertion into the ear and sealing in place, as is illustrated in FIG. 10, is accommodated by digital manipulation utilizing bead 36c while the hand is stabilized against the head.

As is generally illustrated in FIG. 1 in the drawings, an appropriate way of anchoring a device 34 or a device 36 to frame structure 22 may be some suitable form of releasable clamp mechanism which allows snap fitting of a region of the tubular bodies in these two devices to the outer side, or sides, of band 26 in the frame structure. Again, the specific manner of anchoring attachment and stabilization are matters of user choice.

Figure 11:
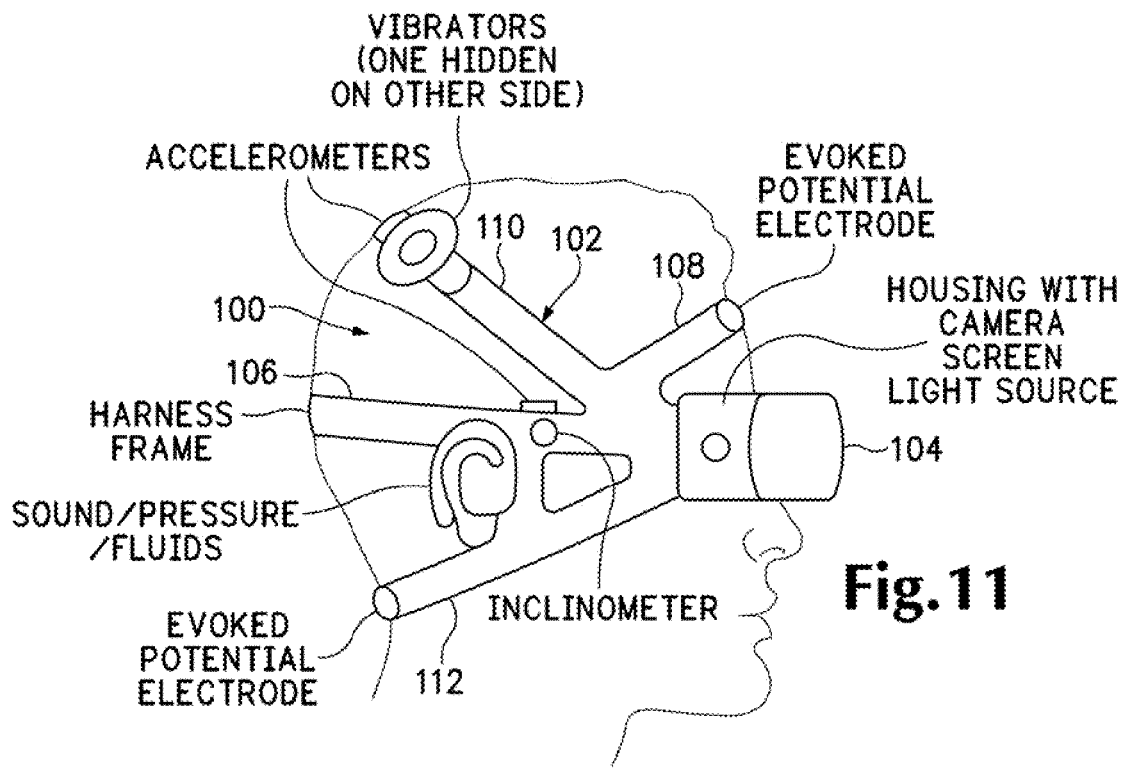
FIG. 11 illustrates a modified form of stabilizing head-gear apparatus constructed in accordance with the invention.

Turning now to FIG. 11, here there is shown generally at 100 a modified form of head-gear apparatus, including a somewhat harness-like frame structure 102 provided in accordance with an alternative form of the present invention. This alternative frame structure, in addition to including a housing 104 which is like previously mentioned housing 24, and an extending looped band 106, which is somewhat like previously mentioned band 26, includes three other strap-like structures 108, 110, 112 which wrap around the forehead, around the upper crown portion of the head, and around the back of the head near the nape of the neck, respectively. FIG. 11 thus illustrates an alternative selected type of stabilizing frame structure which may be employed in conjunction with practice of the invention. When applicable, an ear insert provides further stabilization.

Illustrated generally at the locations labeled in FIG. 11 are various ones of the earlier mentioned types of sensors/stimuli deliverers contemplated for use in accordance with practice of the present invention. In FIG. 11, one will note that a somewhat alternative position, just for illustration purposes, is shown for placement of vibrators, such as previously mentioned vibrators 44a, 44b.

Figure 12:
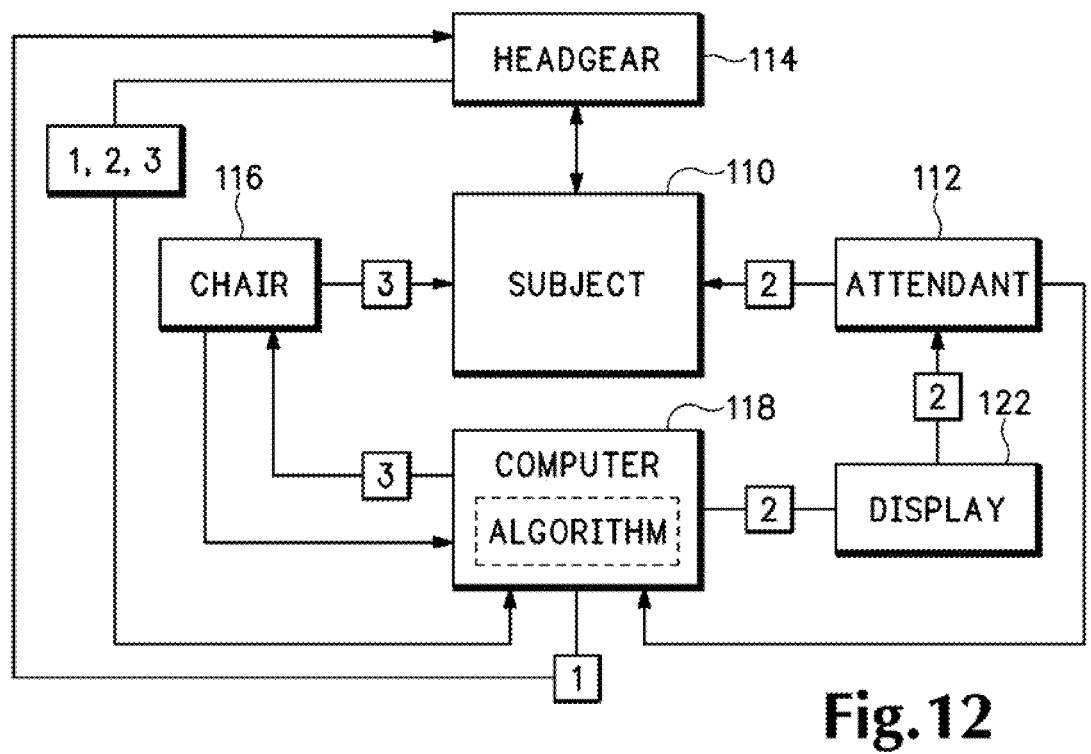
FIG. 12 provides a block/schematic diagram which illustrates, non-exclusively, how the present invention can be invoked as a computer-controlled, feedback-based, expert-trained, vestibular-disorder diagnosis and/or treatment system.

Directing attention now to FIG. 12 in the drawings, here there is shown a block/schematic illustration of a computer-controlled (or driven), feedback-based system implemented in accordance with the invention. This figure provides a graphic picture of how to structure and employ an "expertly trained" algorithm, which may preferably be an adaptive algorithm which can "learn with experience", and/or be retrained over time as desired, in the environment of an appropriate computer, to interact with the stabilized headgear of the invention to furnish effective feedback control over the process which is under way with a subject. One will recall that, earlier in the text herein, several illustrative such feedback situations were generally described.

Specifically shown in FIG. 12 are a subject 110, an attendant system user (typically a physician) 112, Head-stabilized headgear 114 worn by subject 110, an optional maneuvering chair 116, optional in the sense that it may be employed in lieu of using attendant-manual manipulations, an operatively connected computer 118 armed with an appropriate expert-trained algorithm 120, and a display-screen reporting device 122 (which could also employ audible-presentation capability, if desired). Solid lines with arrowheads (for directionality of control and/or action) illustrate existing/potential operative connections between the entities shown in this figure. Dashed lines represent "maneuvering interengagements" enabled between subject 110 and either or both of attendant 112 and chair 116.

In this kind of system, data derived from the headgear (potentially accompanied or augmented by data presented voluntarily by the subject, per se), is fed to the computer, which is, or may, then be engaged in controlling certain headgear stimulators, and furnishing certain readable (text/graphic) information on the display screen. Employing the expert-trained algorithm accessible to the computer, the computer can then engage in relevant feedback activity variously in the forms of: (a) giving instructions to the attendant regarding what to do next in the process under way with the subject; (b) controlling the actions, behaviors, operations, etc. of stimulators incorporated in the headgear, including the deliveries of drugs or other fluids to the subject; (c) controlling the operation of optionally employed chair 116; and so on.

As can be seen, placed in the certain ones of the illustrated connection paths that extend effectively between subject 110, attendant 112, headgear 114, chair 116, computer 118 (and thus algorithm 120), and display 122 are small rectangles bearing different ones of the numbers 1, 2, and 3. The small rectangle present in the path which extends between headgear 114 and computer 120, and which possesses an arrowhead that points to the computer, bears all three of these numbers. The other (six) "small-rectangled" paths are marked each with only one of these numbers.

The collective paths marked "1" define a feedback course wherein detected subject responses cause computer 118 to control/effect the operations of selected stimuli deliverers in the headgear. This "control, etc." can take the forms of adjusting the performances of both the fluid-delivering and the non-fluid-delivering stimulators.

The collective paths marked "2" define a feedback course including the computer, the display, and the attendant, via which the attendant, as an illustration, may be given expert instructions regarding what to do next (typically manually) with respect to the subject.

The collective paths marked "3" define a feedback course including the subject, the computer and the maneuvering chair via which the computer can control the operation of the chair.

Such a feedback system, uniquely enabled by the operational accuracy advantages offered by the present invention, clearly opens the door to making widely available high-level (expertly trained) vestibular-disorder diagnosing and treating capabilities.

Thus, a preferred and one alternative form of head-gear apparatus constructed in accordance with key features of the present invention have been shown and generally described herein, as have also been a recognized useable collection of event sensors and stimulators, all of which have relevance to the diagnoses and treatments of various vestibular disorders. Of key importance, as has been mentioned, is that plural devices in these categories, at least two, from which correlative data is desired to aid in the diagnosis and treatment of vestibular disorders are anchorable in positionally fixed conditions, as described, on and with respect to a head-wearable frame structure, which itself is securable to a subject's head in a fixed and unitized condition with respect to the head.

The utilization, processing and display of linear and angular acceleration data, including gravitation, and of the head-mounted device in general, depends upon the intended use, which falls in three general categories:

(1) Intrinsically-generated position/positioning, as in posturography;
(2) Extrinsically-generated position/positioning, as feedback from manually applied maneuvers; and
(3) Extrinsically-generated position/positioning, as feedback from automated position/positioning apparatus.

Categories (1) and (2) immediately above may require also a geographical direction (north, south, east, west) sensor, such as a magnetic compass input, to portray adequately the spatial position of a subject's head.

What follows now are detailed narratives describing various practices and diagnostic opportunities and advantages that are associated with implementation and use of the present invention.

General Operational and Use Descriptions Relating to Illustrative Practices Employing the Invention The following text generally describes various texts, maneuvers, introductions of stimuli, responses to all of these things, and computer-generated output displays and other computer actions which illustrate practice of this invention in relation to employment of the unique, positionally stabilized gear which is head-mounted on a subject patient in accordance with practice of the invention. Specifically the following text furnishes descriptions of a wide range of operational, use, and resulting output display and calculation activities, that relate to employment of the invention in the exploration of various vestibular-disorder conditions. From this following descriptive material, preferred and various ways of configuring, for example, screen output displays to an operator, such as a physician or clinician, are discussed and suggested, and relevant computer algorithmic architectures are also suggested to those generally skilled in the software art, as such art relates to practice of the invention. No particular display arrangement, or software algorithm protocol, is dictated by the invention. Those skilled in the art will be able readily to link these two considerations to the vestibular investigation needs that they especially wish to address.

Key, however, to the successful employment of the invention is that derived data and implemented stimuli are managed in and by excellent correlation-assuring anchoring of plural selected sensors and stimulators in positionally stabilized conditions on a subject's head. Coupling this important practice to a directly computer-controlled reception and analysis of data removes the possibility of human subjective inattention error, or bias, in detecting important, but often disguisedly subtle, vestibular-response activities which are crucial to consistent, accurate, and near immediate assessment of a patient's particular vestibular situation.

At the lead end of an investigative and/or treatment practice employing the invention, a subject patient is fitted with an appropriately secured head-wearable frame structure, such as structure 22, which itself has an appropriate selection of plural sensors/stimuli devices anchored to it. As has been generally outlined, it is usually with respect to plural categories of properly correlatable, nystagmus- and other-based, data that accurate vestibular-disorder circumstances are discernible and interpretable. Accurate cross-data correlations, and the abilities of detection sensors to provide a clearly readable, "fine-grained" focus on details of vestibular-related behavior as reflected in such data, are of paramount importance to satisfactory and correct vestibular-disorder assessments and treatments, and the structure and practice of the present invention take square and effective aim at these important considerations.

Normally, therefore, the devices which are anchored to the head-wearable frame structure include, in addition to the small video camera which is aimed at the eye, at least the linear and angular accelerometers capable of providing three-dimensional information, and perhaps an inclinometer. Of course, if some stimulus is to be introduced, the appropriate device, or devices, to accomplish that are also anchored in place. Just where these various devices are positioned are purely a matter of professional choice. The frame structure of the invention may, of course, be appropriately configured to accommodate such "choice" locations. For example, linear and angular accelerators are, in most cases, best located at the intersection of the sagital, axial or coronal planes of the head, and at the point maximally distant from the center of rotation for the plane of greatest interest. Generally, this location is at the top, center of the head. According to the invention, these components, once anchored firmly to the frame structure, and with that frame structure fixedly secured against relative movement on the head, all move as a unit with the subject's head, and specifically, without the likelihood of any occurrence of relative motion with respect to one another.

The selected, anchored devices are communicatively connected, in any suitable fashion, to an appropriately algorithmically "armed" computer, which is thus readied to receive data from selected, anchored sensor devices, and which is also, where relevant, readied to deliver control "data" (such as control instructions) to any selected, anchored stimulus-delivery devices. A display monitor arrangement is provided connected to the computer to furnish relevant output information to a system operator, which information can include reports about the conditions and operations of the various sensors/stimulators, as well as diagnostic-aiding information based upon computer assessments and calculations derived from correlated sensor and stimulator activities. The computer may also so report recommended actions to be taken, and can even be structured, if so desired, to "self-implement" certain predetermined types of actions, such as "emergency" actions. Confidence in allowing a computer so to "self-act" is heightened by the confidence which attributable, because of the operation of the present invention, to the position-stabilized accuracy of correlated data which can lead to certain near-immediate conclusions—correct conclusions—about a particular subject's vestibular condition.

With relevant equipment in place, a test/treatment subject is maneuvered passively or actively, or allowed to stand freely, and presented with various stimuli such as air pressure or sound to the ears, or oscillation applied to the head, while eye-movements, postural and other responses thereto are captured by means of the selected sensors anchored to the head-mounted frame structure of the invention.

In a typical situation, responses of the subject's eye movements during testing and treatment are detected in a light-excluding environment in order to minimize suppression of nystagmus by optic fixation (including use of infrared light for video cameras directed at the eyes), and these responses are analyzed electronically, by the connected computer, to record the axis of rotation, angular velocity, linear and angular accelerations and direction of each movement. Test stimuli, as well as response feedback information, may be provided to the test/treatment subject in positional, 2-D visual, 3-D visual, tactile, auditory or electro-vestibular form, including a virtual reality presentation that either simulates the real orientation or purposely distorts the orientation, in order to elicit and determine the subject's response thereto. Various subject-operated levers, switches or adjustable objects, optionally made available, can provide a means to indicate and capture subjective responses.

Response measures are displayed to an operator in the display-provided graphical user interface in a easily understandable, intuitive form (such as a 3-D video image of a model of the semicircular canals oriented at all times according to their actual orientation to gravity of the subject's semicircular canals), along with various levels of information acquired from a knowledge base, and applied to the data obtained from the subject. From this display of stimuli and response measures, modified by intrinsic analysis and compared to a database sample of a normal or abnormal population, the system may assist in diagnosis of the existence, cause (e.g. CNS lesion, non-CNS), localization (e.g. otolithic vs. canalicular, right vs. left, and which specific semicircular canal), and character of the source of vertigo-causing pathology (e.g. free vs. adherent particles). This display of response measures in a highly understandable, intuitive form is derived from any of the following sources:

1) the sensor data relative to the subject's head orientation, at any moment, relative to gravity, and in certain instances relative to geographical direction where a graphical display involves geographical direction;
2) non-positional sensory input to the subject, such as sound or air pressure to the ears, or oscillation to the head;
3) the nystagmus analysis (automated, or by input from the operator); and
4) subjective responses of the subject, related either verbally or by positioning an indicator device to indicate gravity perception.

Such data is typically integrated with data from the following sources:

1) previous maneuvers, responses and nystaginus data from this, or a prior, test;
2) input from the operator, via mouse, touch-screen, joystick, controller or keyboard;
3) the database and algorithms of the intrinsic software with which the computer is armed;
4) subject's medical history;
5) other test devices extrinsic to, but interfacing with, the present system; and
6) other test devices extrinsic to, and not interfacing with, the present system (user input).

Such data is displayed preferably in a graphical user interface as follows.

The virtual 3-D model of the semicircular canals, oriented to indicate the real time orientation in space of the subject's semicircular canals, and their cupulae, is displayed in intuitive form at the graphical user interface (GUI, such as is shown at 52 in FIGS. 1 and 4). For instance, each canal may be color-coded, or the operator may desire to observe the position of only certain semi-circular canals (SCs), with others excluded or translucent. This display greatly assists the operator to comprehend the ongoing relationship of the SCs to gravity, and assists in the repositioning process. This display is generated by simultaneously interfacing the nystagmus analyzer information, which provides the rotational vector of the nystagmus, with the data from the linear acceleration sensors, which provides the orientation of the SCs. When abnormal nystagmus is elicited by position or positioning, and is perceived by the system to be a form that is most likely to be generated in the SC's, the most likely generating SCs are highlighted or otherwise marked (e.g. showing particles descending through the canal), or the other SC's become less marked, or more transparent, in order to allow ease of observation of the offending canal. The apparent, real time, positions of the particles within the SC, or at the cupula, are indicated on the virtual model, taken from a combination of head position and the elicited nystagmus. Also, the operator can have the option of zooming in when needed, as for a better view of the cupular relationship to gravity. The operator can undertake both diagnosis and treatment, monitoring the ongoing orientation in space of the SC's, and the probable relationship of the particles, at all times.

The nystagmus image site depicts the momentary profile of the fast phase of the ongoing nystagmus, as determined by either digital nystagmus analysis or input by the observer. Inasmuch as any movement of the eyeball during a moment in time involves a rotation in a certain plane, and thus upon a certain axis that is perpendicular to that plane, it is possible to depict any such movement by designating the coordinates of the axis and the direction of angular movement about that axis. With the addition of velocity, this can be depicted by a vector representing angular velocity in a certain plane and direction. These are depicted using the right-hand rule, whereby the thumb is directed along the arrow representing the axis of rotation, and the fingers show the direction of rotation.

Thus, the graphical user interface displays the inputs (stimuli), active or inactive, to the subject, including sound to either ear, pressure to either ear canal, head oscillation, visual images and positioning; as well as the subject's responses, after varying degrees of computer analysis to make them more understandable, including graphical analysis of the slow phase velocity of the on-going nystagmus, graphical semicircular canal orientation, and a graphical schematic model of the instantaneous head position. Optionally, the operator can select the maneuvers recommended by the inherent expert system, or can interpose other maneuvers.

This simplification is accomplished by pictorial means, including virtual 3D, which provides an intuitive sense of the momentary spatial relationship of the subject's semicircular canals. Also, the virtual viewpoint for observing the changing spatial orientation of the canals, nystagmus, etc., can, through adjustment of the operator interface display, be either off board (earth-fixed, with the subject changing position) or onboard (head-fixed, with the environment changing position), with either option to be selected by the operator. Means are also be provided for the operator to select different virtual viewing orientations, whether off-board (in relation to a positioning apparatus, if used for positioning) or on-board (in relation to the head and semicircular canals).

In addition to the virtually instantaneous output data, the graphical user interface displays the nystagmus slow phase velocity data in a scrolling manner that allows for improved review and analysis through a greater insight into the present and previous responses. A novel measure of nystagmus activity, the universal slow phase velocity, (USPV) quantifies the nystagmus regardless of its direction. A cursor across the median line can be moved to a particular point and a cursor on the other graph will be moved to the same point in time. The operator can thus move to a previous point in time to review a particular sequence, with the remainder on the graphic display playing out the sequence.

Data from the angular acceleration sensors can also be depicted in the GUI, placed as a separate tracing (distinguished by color or character), in virtual real-time adjacent the SPV (slow phase velocity) tracing, and oriented in their respective vertical and horizontal channels of the SPV display. Thus, the expected normal positioning-induced nystagmus, and after-nystagmus, from angular acceleration of the head can be correlated with the actual nystagmus tracing, and will be less likely confused with particle-induced nystagmus. Also, the timing, direction and velocity of transition and test moves will be more evident. Alternatively, the main nystagmus tracing will be the AUSPV, as described above, in which the angular acceleration effect is extracted from the USPV.

Consistent with the overall intuitive plan of the design of the graphical user interface, ideally there is consistent orientation of all left-right objects and indicators. To accomplish this, the user can select the option of having the eye or eyes viewed upside-down, as the user's view would be if he were standing above the lying patient's head. That position of the user is typical for manually performing the maneuvers.

The intrinsic software may formulate and advise various optional levels of treatment recommendations (e.g. conservative, aggressive or extrinsic to the system). The user is instructed in moving the patient's head relative to gravity, or moving the head through various planes, as is indicated according to both well-known and novel procedures for repositioning of free, adherent or jammed intracanalicular masses. Other test/treatment modalities include the application to the head of oscillation or acceleration-deceleration, the presentation of a visual image and the presentation to the ears of sound or pressure via the head-mounted apparatus with appropriately anchored stimulators.

The operator may interface with the system through monitors, a keyboard, touch-screen, cursor or similar device (as represented by block 50 in FIG. 1), including special controls (e.g. joystick, track-ball, mouse or switches) that actuate, move or control parts of the system.

The system will carry out ongoing monitoring during treatment procedures, and the intrinsic software may recommend, based on the real-time findings, certain immediate modification of the treatment strategy (e.g. a change in the plane of rotation upon perceiving that the nystagmus has converted to a different pattern indicating a conversion of canalithiasis from one semicircular canal to another).

For convenience and economy, the system may provide means to interface with other available systems that are designed to evaluate and/or treat similar disorders (e.g. existing videonystagmography equipment, posturography computers, audiometers, impedance audiometers, evoked response computers, monitors of vital signs, etc.). This interface may be indirect, through the input of the operator, or directly interfaced to the system.

Oscillator/Vibrator Use

The head-mounted apparatus will, when vibration is to be employed, optionally contain two or more oscillators mounted at appropriate angles and locations against the skull behind or around the ears. FIGS. 1 and 11 illustrate two such vibrator deployment conditions. They may be deployed either individually or as a group in concert. They are preferably mounted and deployed in a manner so as to stimulate the cupulae in the canals oriented in the plane of oscillation. This oscillator array is designed either to mobilize intracanalicular dense masses, or to elicit diagnostic responses. The direction of nystagmus elicited, the known oscillator montage used at that time, and the phase relationship of the oscillation signal from the various oscillators, will identify the location of the abnormality. One possible use option involves employing three linear transducers/oscillators (vibration-generating structures) anchored to the head-mounted apparatus, and oriented orthogonally to provide oscillation of the head in several desired directions for lower frequencies of oscillation, and condensation-rarefaction nodes for higher frequencies.

In one approach, each oscillator contains a solenoid that is driven by an applied electrical current, with each solenoid capable of being driven separately. Oscillation driving electrical current is supplied by any suitable electrical power source. Appropriate structure is provided to allow for control of the frequency and intensity of electrical excitation of such oscillators.

Vibration or sound traveling though a liquid or solid moves in a wave that is perpendicular to the direction of travel. The waves move out radially from the source, but in the head there are differences in density that distort the wave somewhat. If there are dense particles to be mobilized in the labyrinth, the wave of oscillation will be most effective in mobilizing them if the wave is traveling tangentially to the portion of a canal containing the particles. In the case of a lithic jam, the jammed particles should be oriented so that movement vertically downward, under the force of gravity, will move them out of the jam, and oscillation should be applied so that the waves travel vertically upward or downward to optimally mobilize them.

For testing the SCs for pathological asymmetry of the SCs, the oscillation should be directed perpendicular to the cupula being tested. As the wave moves the cupula back and forth, the increased firing rate produced in the stimulatory direction will be stronger than the decreased firing rate in the inhibitory direction. But physiologically there is a complementary SC that will produce an equal and opposite effect as a result of a wave in the same direction. Normally, these will cancel each other out so that there is no nystagmus occurring in response to head oscillation. But if the response of one SC is abnormally decreased compared to that of its complementary SC, the oscillatory wave will produce a nystagmus in the plane of the asymmetric SCs, and directed toward the stronger SC of the two. Thus, the use of a phase-directed oscillatory array allows directing an oscillatory wave in any desired direction, and testing of each set of complementary SCs for symmetry. In addition, a cupula weighted by dense particles will also respond more strongly than its complementary SC when oscillation is applied. Thus, this "vestibulosonogram" can locate paretic SCs and weighted cupulae. To actuate SCs in each of the three planes of SC orientation, an oscillator is preferably anchored to each side of the employed head-gear frame structure at an angle to the sagittal plane for the PSCs and ASCs, and at the lateral side of the head for the HSCs.

General Procedure

The basic procedure here begins first with sitting the patient upright but with the head slightly forward (approximately 20-30-degrees) so that the tragal-canthal line is oriented horizontally for calibration purposes. This anatomically represents the plane of the horizontal semicircular canals in relation to the pitch plane. It also indicates the null position for non-zero-buoyant cupulae. Appropriate positional calibration then takes place.

The instruction set for the operator to undertake maneuvers or relay instructions to the patient is in three levels selectable by the operator: (1) Beginner, (2) Intermediate, and (3) Advanced. Another instruction set is available for the patient who is using the system directly. The software will monitor the patient's maneuvers through the position sensors in the head-mounted apparatus, and if at any point the maneuvers are not carried out properly, the operator will be prompted to make corrections.

The process for the system to carry out the basic and pathognomonic test for benign paroxysmal positional vertigo, called the Dix-Hallpike Maneuver, when carried out manually with the subject placed on a table, is now described. Beginning with the seated subject's head placed in the neutral position, or null angle, and after allowing for at least 10-seconds after any prior move, any spontaneous nystagmus is then recorded over the next 10-seconds, noting the axis of rotation (AOR), fast phase direction (FPD) and slow phase velocity of the nystagmus. The head is rotated 45-degrees in the yaw plane to the side undergoing testing, with 5-seconds allowed for cessation of rotation-induced nystagmus, then rotated backward in the pitch plane 120-degrees at a rapid rate (at 120-degrees back, 45-degrees left). After 2-seconds, the eyes are monitored for 20-seconds for one or more forms of nystagmus responses, and diagnostic and treatment conclusions drawn therefrom.

Procedure for Canalith Repositioning

The treatment of choice for classical benign paroxysmal positional vertigo (BPPV) of the posterior semicircular canal is called the Canalith Repositioning Procedure. This and related maneuvers for variations of BPPV are called repositioning maneuvers, and are also known as the "Epley Maneuvers". These are all generally carried out manually with the subject placed on a table. The process for the system to carry out treatment of benign paroxysmal positional vertigo by repositioning maneuvers follows. It presumes that the diagnosis and localization of pathology via the Hallpike maneuver, as performed by the system of the present invention has already taken place. The latency, duration, axis of rotation (AOR), fast phase direction (FPD) and slow phase velocity (SPV) of the nystagmus are duly noted from the prior procedure.

After completion, the display then reports: "Repositioning sequence accomplished, advise repeat. Use oscillation applied to left mastoid process unless patient is nauseated". The sequence is repeated if, at any time during just completed the sequence, a #1 response was noted. If, at any time during the sequence of positions #2 through the final position, the nystagmus reverses, as indicated by reversal of the FPD compared to the FPD in position #1, the display reports: "Repositioning sequence accomplished, reversal of nystagmus noted indicating failure, advise repeat but using 360-degree maneuver in the plane of the left posterior canal."

The second and subsequent sequences are carried out with oscillation applied to the left mastoid area, unless nausea is encountered. The operator has the option to abort the procedure at any point. Severe nausea is a cause to abort the procedure.

Sound and Pressure Tests

In evaluating and managing dizzy patients, there is a also great need for a means to easily and simply test for the abnormal stimulation of the vestibular system by sound and pressure change, also known as Tullio or Hennebert phenomena, and to quantify and standardize the results. These abnormal phenomena have high clinical significance because they are associated with conditions that cause chronic vertigo and/or imbalance in at least 20% of dizzy patients. Moreover, these conditions, once identified, usually respond to treatment.

The Tullio phenomenon was first described by Pietro Tullio, an Italian physician, in 1929. He drilled an opening in the bony semicircular canal of a pigeon and demonstrated that loud sound would then cause nystagmus in the plane of that SC. This phenomenon occurred because the opening in the otherwise solid wall of the semicircular canal allowed the sound waves to traverse the canal and stimulate its sensor, the cupula. It has been inferred that similar softening in the human bony semicircular canal was the mechanism of nystagmus and dizziness that sometimes occurs in humans exposed to loud sound. In clinical application, the accepted definition of the "Tullio phenomenon" has been expanded to include not only nystagmus, but also loss of postural control (imbalance), lightheadedness, nausea, etc., produced when loud sound is presented to the ear. Several disease processes, besides the softening (dehiscence) in a bony semicircular canal, have been implicated as the cause of these signs and symptoms. They include perilymph fistula, subluxed stapes, fibrous adhesions from the stapes to the saccule, dilated saccule, dislocated saccule, hyper-mobile stapes, patent cochlear aqueduct and saccular collapse (atalectasis).

Positive or negative air pressure applied to the ear canal can also create a similar response, called the Hennebert phenomenon. This "pressure test" is often also called a "fistula test", although a positive test has not proven to be actually diagnostic of a perilymph fistula (a leak in the labyrinth), but only suggestive of one.

Although, in any one patient, both sound and pressure stimuli may produce a similar response, sometimes one or the other stimuli produces most, if not all, of the response. Patients demonstrating these phenomena often complain of severe chronic dizziness or imbalance, aggravated by sound, physical activity or changes in ambient air pressure, as in altitude change.

An informal poll of otolaryngologists indicates that although they were informed of the Tullio and Hennebert tests in their training period, they seldom perform these tests because they are hard to quantify and interpret, they are not standardized and they may make the patient nauseated. Much of this disaffection occurs because these tests are usually, and inadvertently, done improperly, and with inadequate equipment. For instance, these tests are typically carried out by sitting the test subject down and presenting the test ear with sound from a tuning fork, or pressure from a squeeze bulb, and observing the eyes for induced nystagmus. But, this is irrational and counter-productive in many respects. First, in view of the fact that the most common characteristic of the Tullio and Hennebert responses is a decrease in postural control (increased imbalance), it makes no sense to sit the patient down during the test. Second, tuning forks and squeeze bulbs are poorly quantifiable stimuli. Third, watching the eyes seldom results in a positive, observable response. These factors, plus lack of standardization, lead many physicians to doubt the validity and value of the sound and pressure tests. But the problem is in the way they carry out the tests.

This fact has become clear in testing and treating a large cohort of dizzy patients in an unpublished study at the Portland Otologic Clinic. It was demonstrated that if, instead, the dizzy patients are tested while standing freely and are observed for a sudden decrease in balance, an abnormal response will be elicited at least 20-times more often than a response of nystagmus. Further, in patients that have shown a sudden decrease in balance, with or without nystagmus, in response to sound or pressure in one ear, treatment of that ear by surgery or chemical perfusion has resulted in amelioration or resolution of their symptoms in a high proportion of cases. In addition, in using quantifiable stimuli, improvement could be monitored over time.

Thus, a positive response to one or both of these tests, when performed in the appropriate manner, is an indication of an abnormal focus of irritability in the ear that is probably the source of their symptoms. Not uncommonly, a positive Tullio or pressure test is the only positive finding in dizzy patents, so failure to carry out these tests, and in the proper manner with the subject standing, can result in entirely missing the diagnosis.

Therefore, this pair of tests should be carried out in the proper manner on every dizzy patient, first as a screening mechanism, second as a definitive diagnostic and localizing test, and finally as a means to monitor their response to treatment.

A somewhat similar test system is generally known as one which implements the "platform fistula test"(PFT). The test subject is placed on a force platform that records his/her ongoing center of gravity, while positive and negative air pressure, at a set intensity, is presented to the test ear in regular, alternating fashion for a preset period of time.

One disadvantage of this system is that, in many subjects, pressure at this obligatory stimulus time and intensity often continued long after enough information for a positive response was obtained, thus unnecessarily creating severe nausea that could require days to recede, and was probably a major reason for the loss of popularity of the test. This is avoided in the use of the present invention by starting the sound or pressure stimulus train at a low level, increasing it gradually, and stopping it as soon as a measurable response is detected. Thus, a subject receives a minimal stimulus.

Another problem with the PPT was that the alternating pressure stimulus was expected to create a synchronized postural sway response. But, in actuality, because the subject's response was often delayed or because the subject often gave voluntary counteractive responses, the sway response was often quickly thrown "out of sync" with the stimulus, creating a false negative test. Or, occasionally, the subject's natural sway rate would happen to be "in sync" with the stimulus, creating a false positive. Also, the Neurocom apparatus could measure sway response in only the anterior-posterior direction, neglecting responses directed laterally.

The present invention can avoid these problems by presenting a stimulus with the timing varying at random and that will leave ample time between stimuli for a delayed response, and the measured sway responses in all directions.

Ear pieces or head sets are common means of presenting sound or pressure to the external canals of the ear, and presently take many forms. However, the present invention provides that, for convenience and saving time, both sound and/or pressure may be presented via the same device structured so that one size fits all. Only one application of the device to the ears is required, and it can be applied to both ears at once. The critical factors are that there be an air-tight pressure seal (hermetically sealed) and that the airway be patent, allowing the pressure and sound to pass unimpeded. The only earpiece presently in use that satisfies most of these criteria is that which is commonly used in impedance audiometry, and consists of a soft plastic spherical insert with a small opening. This must be inserted into the ear by pulling back on the pinna so that it passes the posterior cartilaginous lip, which then holds it in place. The disadvantages of this arrangement are that insertion must be done in each ear separately, and different sizes are necessary. The "mushroom tip" of the modem stethoscope configuration, which is designed for listening to sounds with the earpieces in the ear of the listener, somewhat solves these problems by having a soft ear tip under inward pressure, but in practice these tips often do not easily become hermetically sealed (air-tight), nor do they always allow patency of the airway.

Typically, a stethoscope user soon learns to adjust the ear pieces accordingly, sometimes with difficulty, by listening for an adequate decrease in ambient sound, representing air-tightness, and for adequate transmission of sounds from the end-piece, representing airway patency. The main disadvantage of the various earpieces in stethoscopes are that the tip is round shaped in cross-section, whereas the meatal opening of the ear canal is usually oblong. Another problem is that many meati make a posterior bend of the anterior wall just inside the meatus, so that obstruction of the tip opening occurs when it is pushed against the bending anterior wall. Some ears have a convex posterior lip that easily obstructs the opening of the ear tip.

Thus, to solve these problems, the head-mount apparatus of the present invention accommodates a device with a tip that is oblong and tapered so as easily to enter the meatus by slipping past the posterior lip and pushing it backwards under the medial pressure of the arms. This device has a cruciate opening that resists collapse under external pressure, and that thus maintains airway patency, even if the tip is pushed against a posterior-bending anterior wall. In addition, the proposed device preferably quickly senses and signals to the operator if hermeticity or airway patency are not being accomplished, so that readjustment can be made in the earpiece position. It accomplishes this by applying a slight alternating air pressure to the system during insertion, and by sensing a lack of hermeticity through noting whether the pressure is maintained, and assuring airway patency by noting whether there is the normal compliance as is provided by the usual 6-square centimeters of air space of the ear canal.

Further describing sound and pressure practice employing the stabilized head-gear of the present invention, two of the just-mentioned, specially designed earpieces can be quickly applied to a patient's ears, with a tight seal but with open passage to the ear canal. These earpieces are connected to tubes that can carry sound and pressure. The tubes lead from a unit that introduces a measured amount of sound (an electronic signal generator) or pressure (a cylinder and actuator) to either ear. Further, this device can detect a poor seal or obstructed passageway, notifying the operator to make necessary adjustments. The stimulus-response portion of the device, the base unit, can be hand-held, or can be placed on a small portable table. The stimulus (sound or pressure) is selected and triggered from this unit, and responses displayed and recorded, or can be scanned and digitally processed for analysis. Detection of the patient's response of decreased balance (postural destabilization) or nystagmus is accomplished by means of the head-mounted apparatus containing an inclinometer to detect increased sway or fall, and also containing a small infrared camera trained on the eye to detect nystagmus. The graphic user interface displays stimulus and response data. The output of the inclinometer and infrared camera leads to a small display wherein one can readily detect changes in postural control, and to a recording and analysis function respecting nystagmus. This activity is displayed and preferably printed out, correlating the stimulus presentation with the subject's responses. Computer-managed digital storage documents the nystagmus findings.

Sound and pressure in this situation are presented separately, in accordance with use of the present invention, and in a train with ascending intensity to each ear in turn, such that the operator or a computer can discontinue the train of stimuli as soon as a significant response is observed and thus not allow the stimuli to create excessive nausea that would interfere with the further conduct of the test and produce nausea in the patient.

A novel test for malingering during the procedure can be accomplished by utilizing a phenomenon which involves the fact that, although subjects can perceive the pressure sensation in their ears, they have difficulty distinguishing the difference between positive and negative pressure. In addition, when there is a sway response to pressure, its direction (right-left, back-forward) is typically in the opposite direction when responding to negative pressure than when responding to positive pressure. Thus, the momentary direction of sway should consistently correlate with the momentary condition of the pressure stimulus. Also, the direction of sway induced by the negative pressure is typically in the same direction as that induced by sound. The momentary decision to give a positive or negative stimulus will be randomly selected by the embedded software, so even if those subjects that were intent on malingering were to know exactly what do to "beat the

Intratympanic Perfusion—One-Step Insertion Catheter

Intratympanic perfusion of drugs for treatment of inner ear conditions was popularized the 1970's in Europe with the treatment of Meniere's disease with intratympanic aminoglycoside antibiotics. This route of administration, with various drugs, has since gained wider utilization in the treatment of many other ear conditions as well, including tinnitus, sudden hearing loss, and various forms of labyrinthine dysfunction. Medications typically used include aminoglycosides, corticosteroids and local anesthetics. Anticipated delivery of other medications by this route has undergone widespread discussion.

Recent studies have shown that there is a blood-labyrinth barrier similar to the blood-brain barrier, such that very little of most medications delivered systemically (oral, IV, etc.) is transported to the inner ear via the blood circulation. Thus, to accomplish a therapeutic concentration of some medications within the inner ear when delivered via the systemic route, high concentrations of the drug over sustained periods of time may be necessary, increasing the risk of systemic side effects. Also, one may desire to direct the drug to only one ear.

If a solution containing the drug molecules is placed into the middle ear and is allowed to remain for a period of time, a portion of the molecules will be absorbed into the inner ear, probably mainly by way of the round window, and probably mainly by diffusion through the round window membrane. This has proven to be a much more effective means to deliver drugs to the inner ear. One advantage of intratympanic delivery is that it provides a method of obtaining a high concentration of drug in the inner ear while causing a minimum of systemic concentration of the drug, thereby minimizing systemic side effects.

Certain drugs, such as aminoglycosides (gentamicin, streptomycin, etc,) are relatively toxic, and are given intratympanically for their ototoxic effect, which tends to be more specific for the vestibular endorgans, but can damage the hearing if given at too high a dose. Thus, titration of the inner ear dose is often desired so as to affect only the vestibular endorgan and not damage the hearing, and often to affect the vestibular endorgan only partially; but intratympanic perfusion at high concentration by a single, or a series of single, injections has proven to be severely inconsistent. Intratympanic perfusion over an extended period of time, with the aminoglycoside concentration at low levels, has proven to be a much more consistent mode of delivery.

Other drugs, such as corticosteroids (dexamethasone, methylprednisolone) are far less toxic, and are given for their anti-inflammatory effect, but need to reach relatively high inner ear doses to be effective. Here the goal is usually to administer the maximum dose possible to the inner ear. This can be accomplished by intratympanic perfusion of a moderate concentration over an extended period of time.

Intratympanic perfusion is generally accomplished in several ways. The most common method is to make a small incision in the tympanic membrane, and then to insert a narrow, blunt-end, needle-catheter on a syringe and inject the solution. The patient is then instructed to lie with that ear up for a period of time varying from 30- to 120-minutes.

This has proven to have an inconsistent effect for aminoglycosides, and inadequate effect for corticosteroids.

The amount of absorption of the drug molecules through the round window, and hence the dose of the drug reaching the inner ear structures, is approximately proportional to the concentration of the drug in contact with the round window membrane, multiplied by the time it remains in contact with the round window membrane at said concentration.

The middle ear cavity can hold approximately 0.5-cc of fluid. Its outer surface is lined by mucous membrane, which absorbs medication molecules from the middle ear. If a solution (perfusate) containing medication is thus placed in the middle ear cavity, the molecules of that medication in the solution will diffuse over time into the surrounding tissues, including the round window membrane. The round window represents only a small proportion of surface area of the surrounding tissues, less than 2%, therefore only a small portion of the molecules of drug will diffuse through the round window into the inner ear. On the other hand, because the volume of the inner ear is small, relatively few molecules of medication are needed to obtain a therapeutic concentration in the inner ear.

Molecules of drug diffuse out of the solution into the surrounding tissues so that concentration of drug in the solution becomes less with time, following an asymptotic curve. The applicant's studies indicate that the half-life of drug molecules in a solution lying in the middle ear cavity is approximately 5-10-minutes. If there is any positive pressure build-up in the middle ear by the injected fluid, it will be forced down the Eustachian tube to be absorbed systemically, or out to the external auditory canal where it is not absorbed systemically. Some Eustachian tubes are weak or patent, and intratympanic solutions will traverse the tube without positive pressure. Therefore, the solution often does not stay in the middle ear as intended for the prescribed time.

Thus, if the typical protocol for single injection is followed, and 0.5-cc's are infused into the middle ear and the patient lies with the ear upward for 30-120-minutes, the time past 10-15-minutes is at a much lower concentration, and therefore not effective. If, instead, infusions are undertaken every 5-minutes for 30-minutes, the constant replenishing of the concentration will result in 3 times the amount of the drug reaching the inner ear during that time. If replenishing the perfusate is carried out constantly during this time, the effect is even greater. Thus, the ideal infusion method for maximum concentration reaching the inner ear would involve a frequent or constant replacement or replenishing of the drug. This can often be accomplished by continuous perfusion with an indwelling catheter to obtain therapeutic doses in over minutes to hours. In this way, the patient can be treated maximally in the office situation, not having to undergo infusion at home nor to return frequently for more infusions.

Intratympanic delivery of drugs has been accomplished in the past principally by making a small incision in the anesthetized tympanic membrane (ear drum), inserting a needle or catheter through the incision into the middle ear, infusing the drug in solution and allowing it to be absorbed into the inner ear, probably mainly by way of the round window membrane. Other methods have included placing an incision or implanted tube in the tympanic membrane and then having the patient self-dispense the drug into the external ear canal whereby it is intended to pass through the opening into the middle ear, and thence the inner ear. This has the disadvantage that infectious debris can be carried into the middle ear from the external canal, with the risk of creating a middle ear infection, and passage of the liquid into the middle ear is inhibited by the surface tension of the liquid. These problems have been partially solved by inserting a wick between the external ear canal and the middle ear, but this method has the disadvantages of possible patient noncompliance, errors in following directions, confusion of medications, failure of some or all of the instilled drops to reach the wick, infections and chronic perforations due to the extended use of the wick.

Proposed for use with the stabilized head-gear of the present invention is a unique fluid-flow structure which takes the form of a small beveled trocar on the delivery end of an elongate malleable tubular body. A digital-manipulation spheroidal enlargement (also called herein a manipulation bead) is provided on this body to ease and facilitate the process of ear insertion. The beveled, or sharpened, trocar is intended for placement through the tympanic membrane, and a 2-lumen tubular structure is provided in the tubular body extending out the external ear canal preferably to two pouches in a fluid-retaining reservoir, one for input and one for output.

The operator inserts the ear trocar through the anesthetized ear drum membrane—the trocar making its own incision of exactly the right size so it will minimally leak into the external canal. The operator injects liquid molding material into the outer canal and concha, and around the outer tube, where it quickly cures and hardens to stabilize the tube relative to the ear. Between the handle and the trocar, in mid-canal, the tube is made of a suitable malleable metal in order to absorb sound and shock the might be applied to the lateral end of the catheter. Fluid inflow is controlled preferably by a small pump or valve suitably connected to the inflow tube.

A reservoir is preferably stably connected to the head-strap portion of the head-mounted apparatus. Delivery occurs by several alternative means. In one, the return flow of the perfusion liquid to the return pouch of the reservoir is absorbed by a large piece of a compressed, absorbent material within the pouch that expands when wet, and that, when filled, can force out the remaining treatment liquid in the reservoir. Alternatively, a conductive member for receiving electrical potentials from ear tissues is affixed to the trocar and leads to the headset. This apparatus is surgically inserted so that the trocar opening is placed within the middle ear deep to the tympanic membrane. As the 2-lumen tubing extends out the external ear canal to the reservoir, nodules on the tubing near the external meatus act to hold the trocar in place, with the help of retaining material placed in the meatal area, such as expanding sponge material or molding material.

Acting on the flow in the tubing near the reservoir is an electronically-activated valve that can control the flow of perfusate to the ear. In one configuration, the valve is controlled by the computer, which monitors (via the IR goggle cameras) the change in nystagmus produced by the medication in the inner ear, and controls fluid input thorough electronic pumps or control valves. The perfusate can be tagged with nystagmus-producing or ameliorating drugs, such as lidocaine.

An example of the application of this catheter system is in bilateral titration of labyrinthine anesthesia. There are several conditions (tinnitus, certain vertigo conditions) where the treatment of an inner ear by unilateral local anesthesia such as lidocaine and Marcaine is beneficial. These medications cannot be given systemically in high enough dosage to be effective without affecting safety. However, a high enough dosage can be delivered to the inner ear by perfusing the solution into the middle ear and allowing it to diffuse through the round window membrane into the inner ear. But, a problem with using this procedure unilaterally with a local anesthetic is that the anesthetic shuts down the labyrinthine sensors unilaterally, creating a large labyrinthine asymmetry. The patient will then develop a severe nystagmus and become very dizzy and nauseous. However, this can be prevented by perfusing both ears simultaneously, and titrating so that each balances the other out, and each side is shut down equally. That balance may be difficult to accomplish however, because a given amount of solution in a middle ear may vary in effectiveness due to anatomical factors, pathology, etc. This problem can be overcome with use of the present invention by monitoring the nystagmus with IR videography while titrating the two sides against each other. When the effect of the anesthetic becomes unbalanced, the nystagmus will start to beat toward the less anesthetized ear, whereupon a catch-up or larger dose can be delivered to that ear. This monitoring requires IR videography because asymmetry must be detected early, and acted upon before the patient gets nauseated.

The invention, and its use, are thus now fully described. Subtle data errors which can arise in relation to sensors and stimulators that are not positionally stabilized relative to a subject's head are avoided by use of the invention. Accordingly, illusive sources of vestibular disorders are not masked behind data containing relative-motion errors. Stimuli of sound and fluids can be administered through novel deliverers especially structured and suited for positional anchoring and stabilizing on the wearable head frame structure of the invention.

Interesting and valuable extension applications for this invention include implementation of a stabilized headgear/computer-based system that can be employed as training equipment for use in expanding the practical knowledge in the medical field regarding the diagnosis and treatment of vestibular disorders. In this context "virtual subjects" can be created as training data bases derived from "real-life" data acquired from prior use of the stabilized headgear of the invention.

The invention also opens the door to the provision of "expert" self-treatment systems which can be made available to qualifying subjects/patients for self-use.

Many other vestibular-field options are made possible by the invention, and those skilled in the art will recognize that these other options, including variations and modifications, in the selection and use of various styles of stabilizing frame structures, can be created and employed well within the spirit of the present invention.

I claim:

1. A method for preparing vestibular-response data for useful analysis regarding a desired diagnosis and prospective treatment of a subject's related vestibular disorder comprising:

coupling an eye-enclosing, ambient light-excluding flame structure to and in a positionally stable non-relative-motion condition with a subject's head, wherein the frame structure includes a likewise positionally stable electronic video image-collecting sensor apparatus anchored thereto and positioned to observe one or both of the subject's eyes;

applying to the subject a vestibular-response-inducing stimulus and producing a data record corresponding to the applied stimulus;

collecting from the subject, concurrently with the applied stimulus, data indicating the subject's detectable vestibular-response relative to the applied stimulus;

collecting from a geographical direction sensor data indicating a spatial position of the subject's head;

producing a record corresponding to the vestibular-response data, wherein the vestibular-response data am thereafter selectively correlateable, whether individually or plurally, with respective corresponding contemporaneously-produced data of the stimulus data record; and electronically analyzing, by a computer, the vestibular-response data and the geographical direction sensor data relative to one or more characteristics of the applied stimulus to evaluate the subject's related vestibular disorder.

2. The method of claim 1, wherein the collecting data indicating the subject's detectable vestibular-response comprises capturing, utilizing the electronic video image-collecting sensor apparatus, images of subject nystagmus behavior.

3. The method of claim 2, further comprising:
utilizing the electronic video image-collecting device to observe nystagmus behavior while simultaneously delivering selected liquid to the ear employing a fluid-flow structure coupled with the ear.

4. The method of claim 3, further comprising:
providing a controller for controlling the delivery of liquid to the ear by the fluid-flow structure, and affecting the controlling operation of the controller by utilizing data derived from observations of simultaneously observable nystagmus behavior made by the electronic video image-collecting device.

5. The method of claim 2, further comprising:
identifying, by vector analysis of the collected nystagmus data relative to contemporaneously produced stimulus data, one or more originating semicircular canals of an observed nystagmus response.

6. The method of claim 1, wherein the stimulus is applied to the subject's head by a stimulus apparatus operatively coupled in a non-relative motion condition with the subject's head.

7. The method of claim 6, wherein the stimulus is applied using a stimulus apparatus comprises one or more selected from among (a) a sound deliverer, (b) an air-pressure modifier operatively coupled with the ear, (c) a fluid-flow structure operatively coupled with the ear, (d) a light-emitting structure, (e) a visual image-presenting structure, (f) an evoked-potential electrode structure, (g) a galvanic stimulus structure, (h) a caloric stimulus structure, and (i) a vibration-generating structure.

8. The method of claim 1, further comprising:
depicting at a display device a graphical representation of the subject's eye, wherein the graphical representation depicts movement of the subject's eye corresponding to actual movement of the subject's eye in one or more of a lineal axis and a rotational axis.

9. The method of claim 1, further comprising:
utilizing the stimulus data, differentially identifying and isolating physiologic components of the collected vestibular-response data from any pathologic components thereof.

10. The method of claim 1, wherein the vestibular-response-inducing stimulus comprises altering a spatial orientation of the subject's semicircular canals relative to a previously existing spatial orientation thereof along one or more axes of movement.

11. The method of claim 1, further comprising:
depicting at a visual display device a graphical representation of an actual spatial orientation of one or more of the subject's semicircular canals, wherein a change in the depicted spatial orientation corresponds to a change in the actual spatial orientation of the subject's one or more semicircular canals.

12. The method of claim 1, enabling selection of a graphically-depicted, time-specific component of recorded data corresponding to a nystagmus response, wherein the selection causes a display device to graphically depict a time-specific orientation of one or more of the subject's semicircular canals sensed contemporaneously with the nystagmus response component.

13. The method of claim 1, wherein either or both of applying the vestibular-response-inducing stimulus and collecting the vestibular-response data is performed under computer control.

14. The method of claim 1, further comprising:
securely coupling plural devices with a retention structure and securely coupling the retention structure with the subject's head, wherein appreciable relative motion is prevented between the plural devices, between the retention structure and the plural devices, and between the retention structure and the subject's head, and wherein the plural devices are selected from among vestibular-response-inducing devices and vestibular-response sensing devices.

15. The method of claim 1, further comprising:
providing, by a computing device, an instruction indicating a target orientation for one or more of a subject's semicircular canals, and repositioning the subject to achieve the target orientation.

16. The method of claim 1, further comprising:
receiving an instruction from a computing device indicating a target orientation for one or more of a subject's semicircular canals, repositioning the subject to achieve the target orientation, and receiving confirmation from the computing device that the target orientation has been achieved.

17. The method of claim 1, wherein the electronic video image-collecting device is an infrared camera.

* * * * *

UNITED STATES PATENT AND TRADEMARK OFFICE
CERTIFICATE OF CORRECTION

PATENT NO.        : 7,892,180 B2
APPLICATION NO.   : 11/714459
DATED             : February 22, 2011
INVENTOR(S)       : John M. Epley It is certified that error appears in the above-identified patent and that said Letters Patent is hereby corrected as shown below:

In the Claims:

Column 34, claim 1, line 47, "flame" should be changed to --frame--; line 63, "am" should be changed to --are--.

Signed and Sealed this
Twenty-sixth Day of April, 2011

David J. Kappos
*Director of the United States Patent and Trademark Office*